(12) United States Patent
Swanson et al.

(10) Patent No.: US 8,399,630 B2
(45) Date of Patent: Mar. 19, 2013

(54) ENGINEERED ANTI-IL-13 ANTIBODIES, COMPOSITIONS, METHODS AND USES

(75) Inventors: Ronald V. Swanson, San Diego, CA (US); Ellen Chi, San Diego, CA (US); Gopalan Raghunathan, San Diego, CA (US); Shanrong Zhao, San Diego, CA (US); Johan Fransson, San Diego, CA (US); Wendy Cordier, San Diego, CA (US); Hong Mimi Zhou, San Diego, CA (US); Juan C. Almagro, Radnor, PA (US); Linus Hyun, Radnor, PA (US); Jill Giles-Komar, Radnor, PA (US); Karyn T. O'Neil, Radnor, PA (US); Jill M. Carton, Radnor, PA (US); Alexey V. Teplyakov, Radnor, PA (US); Yiqing Feng, Radnor, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 0 days.

(21) Appl. No.: 13/058,453

(22) PCT Filed: Aug. 11, 2009

(86) PCT No.: PCT/US2009/053425
§ 371 (c)(1),
(2), (4) Date: Feb. 10, 2011

(87) PCT Pub. No.: WO2010/021874
PCT Pub. Date: Feb. 25, 2010

(65) Prior Publication Data
US 2012/0045438 A1    Feb. 23, 2012

Related U.S. Application Data

(60) Provisional application No. 61/090,472, filed on Aug. 20, 2008, provisional application No. 61/097,232, filed on Sep. 16, 2008.

(51) Int. Cl.
*A61K 39/395* (2006.01)
*C07K 16/24* (2006.01)
*C07H 21/04* (2006.01)
*C12N 15/63* (2006.01)
*C12P 21/06* (2006.01)

(52) U.S. Cl. ............... 530/388.1; 530/387.3; 530/387.9; 530/388.23; 424/141.1; 424/145.1; 435/326; 435/335

(58) Field of Classification Search .................. None
See application file for complete search history.

(56) References Cited

U.S. PATENT DOCUMENTS

| | | | |
|---|---|---|---|
| 5,596,072 A * | 1/1997 | Culpepper et al. | 530/351 |
| 5,652,123 A | 7/1997 | Caput et al. | |
| 5,710,023 A | 1/1998 | Collins et al. | |
| 6,143,871 A | 11/2000 | Bonnefoy et al. | |
| 6,214,559 B1 | 4/2001 | Collins et al. | |
| 6,268,480 B1 | 7/2001 | Collins et al. | |
| 6,472,147 B1 | 10/2002 | Janda et al. | |
| 6,743,604 B1 | 6/2004 | Bonnefoy et al. | |
| 6,881,557 B2 | 4/2005 | Foote | |
| 7,078,494 B1 | 7/2006 | Collins et al. | |
| 7,282,206 B2 | 10/2007 | Wynn et al. | |
| 7,501,121 B2 | 3/2009 | Tchistiakova et al. | |
| 7,553,487 B2 | 6/2009 | Collins et al. | |
| 7,619,070 B2 | 11/2009 | Cardarelli et al. | |
| 7,674,591 B2 | 3/2010 | Collins et al. | |
| 2003/0103978 A1 | 6/2003 | Desphande et al. | |
| 2007/0048785 A1 | 3/2007 | Lin et al. | |

FOREIGN PATENT DOCUMENTS

| | | |
|---|---|---|
| WO | WO 01/23410 A2 | 4/2001 |
| WO | WO 02/101629 A1 | 12/2002 |
| WO | WO 2005/007699 A2 | 1/2005 |
| WO | WO 2005/062967 A2 | 7/2005 |
| WO | WO 2005/079755 A2 | 9/2005 |
| WO | WO 2005/121177 A2 | 12/2005 |
| WO | WO 2005/123126 A2 | 12/2005 |
| WO | WO 2006/055638 A2 | 5/2006 |
| WO | WO 2006/085938 A2 | 8/2006 |
| WO | WO 2007/045477 A2 | 4/2007 |
| WO | WO 2008/052108 A2 | 5/2008 |
| WO | WO 2008/127271 A2 | 10/2008 |
| WO | WO 2009/085462 A1 | 7/2009 |

OTHER PUBLICATIONS

US 5,783,191, Jul. 1998, Browne et al. (withdrawn).
Blanchard C. et al., "Inhibition of human interleukin-13-induced respiratory and oesophageal inflammation by anti-human-interleukin-13 antibody (CAT-354)", Clinical & Experimental Allergy. 35(8):1096-1103 (2005).
Teplyakov et al., "Epitope mapping of antiI-IL-13 neutralizing antibody CNTO607", Journal Mol. Biol., 389, pp. 115-123 (2009).
Zhu et al., "Pulmonary expression of interleukin-13 causes inflammation, mucus hpersecretion, subepithelial fibrosis, physiologic abnormalities, and eotaxin production" Journal of Clinical Investigation, 103, pp. 779-788 (1999).
Doucet et al., "IL-4 and IL-13 specifically increase adhesion molecule an dinflammatory cytokine expression in human lung fibroblasts", International Immunology, 10(10), pp. 1421-1433 (1998).
Doucet et al., "IL4 and IL13 bind to different types of functional OL4/1L13 receptors on human lung fibroblasts", Meeting Information Meeting on new therapeutic Approaches for Allergic Diseases of the Respiratory Tract, Paris, France; Apr. 1-4, 1998.

(Continued)

*Primary Examiner* — Bridget E Bunner
*Assistant Examiner* — Fozia Hamud
(74) *Attorney, Agent, or Firm* — Brian C. Carey

(57) ABSTRACT

The present invention relates to engineered antibodies immuno specific for human interleukin-13 (IL-13) protein or fragment thereof, as well as methods of making and using thereof, including therapeutic indications.

5 Claims, 12 Drawing Sheets

OTHER PUBLICATIONS

Figure 2:
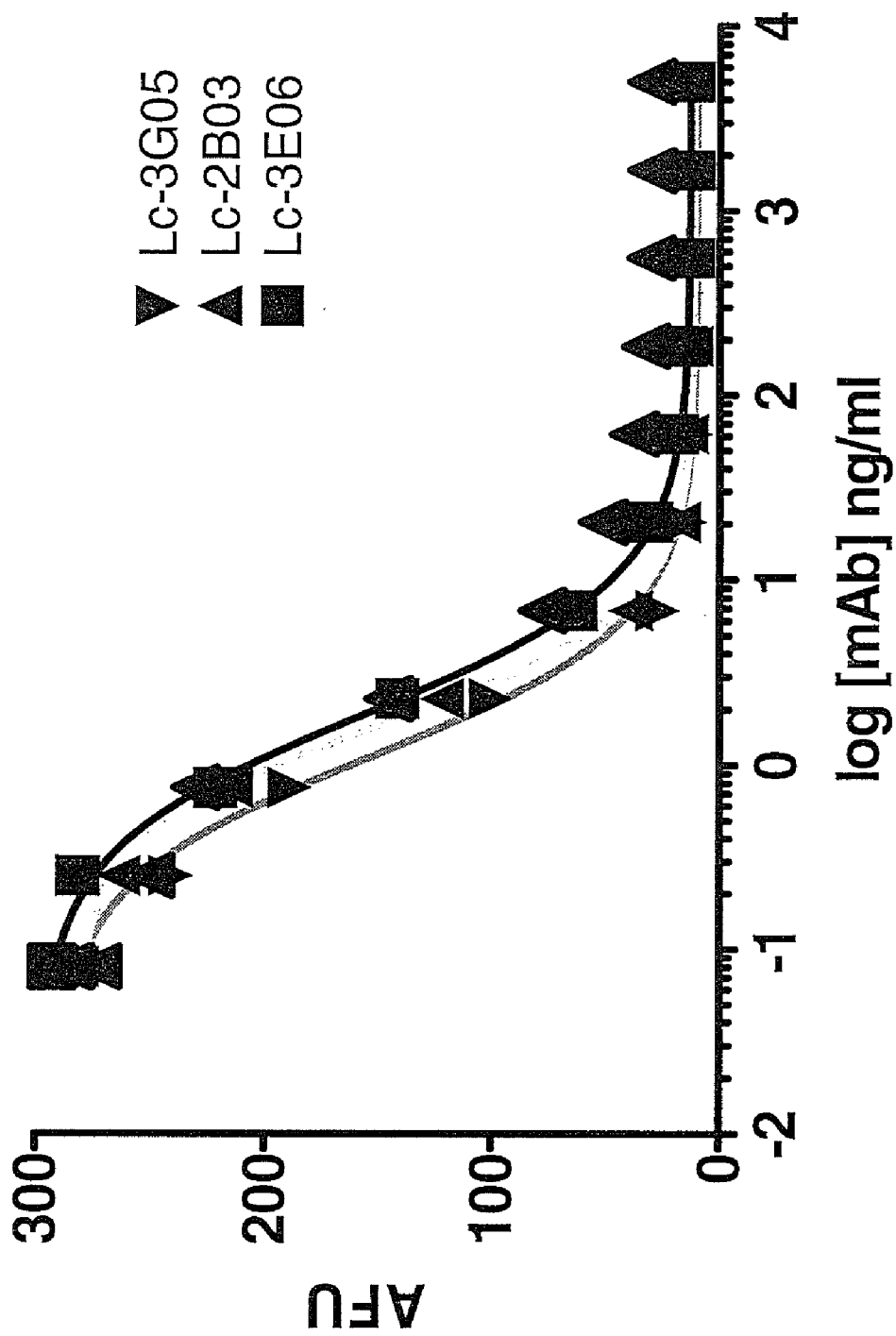

Doucet et al., "Interleukin (IL) 4 and IL-13 Act on Human Lung Fibroblasts", J. Clin Invest., 101(10), pp. 2129-2139 (1998).
Kroegel et al., "Eosinophil priming and migration in idiopathic pulmonary fibrosis", Eur Respir J. 11, pp. 999-1001 (1998).
Hancock et al., "Production of Interleukin 13 by Alveolar Macrophages from Normal and Fibrotic Lung", American Journal of Respiratory Cell and Molecular Biology, 18(1), pp. 1-6 (1998).
ICD Code: 493.0 Extrinsic asthma; occupational asthma; exercise induced asthma, TDRdata.com, 2005.
Van Der Ploeg et al., "IL-13 over-expression in skin is not confined to IgE-mediated skin inflammation", Clin Exp. Immunol, 109, pp. 526-532 (1997).
Li et al., "Effects of Th2 Cytokines on Chemokine Expression in the Lung: IL-13 Potently Induces Eotaxin Expression by Airway Epithelial Cells", The Journal of Immunology, 162, pp. 2477-2487 (1999).
Bost et al., "In vivo treatment with anti-interleukin-13 antibodies significantly reduces the humoral immune response against an oral immunogen in mice", Immunology, 87, pp. 633-641 (1996).
Virchow et al., "Inflammatory determinants of asthma severity:mediator and cellular changes in bronchoalveolar lavage fluid of patients with severe asthma", J. Allergy Clin Immunol., 98 (5 Pt 2):S27-33 (1996).
Van Der Pouw Kraan et al., "The role of IL-13 in IgE synthesis by allergic asthma patients", Clin Exp Immunol, 111, pp. 129-135 (1998).
Barnes et al., "Inflammatory mediators of Asthma: An Update", Pharmacological Reviews, 50 (4), pp. 515-596 (1998).
Punnonen et al., "The relative contribution of IL-4 and IL-13 to human IgE systhesis induced by activated CF4+ or CD8+ T cells", J. Allergy Clin Immunol., 100 (6) part 1, pp. 792-801 (1997).
Graves et al., "A cluster of seven tightly linked polymorphisms in the IL-13 gene is associated with total serum IgE levels in three populations of white children", J Allergy Clin Immunol 105: pp. 506-513, (2000).
Heinzmann et al., "Genetic variants of IL-13 signalling and human asthma and atopy", Human Molecular Genetics, 9: pp. 549-559, (2000).
Howard et al., "Identification and Association of Polymorphisms in the Interleukin-13 Gene with Asthma and Atopy in a Dutch Population", Cell Mol. Biol. 25: pp. 377-384, 2001.
Padlan et al., "Identification of specificity-determining residues in antibodies", FASEB J 9: pp. 133-139, (1995).
Almagro, Juan C., "Identification of differences in the specificity-determining residues of antibodies that recognize antigens of different size: implications for the rational design of antibody repertoires", J Mol. Recognition 17: pp. 132-143 (2004).
Almagro et al., "Design and validation of a synthetic $V_H$ repertoire with tailored diversity for protein recognition", J. Mol Recognition 19: pp. 413-422 (2006).
Fransson et al., "Human framework adaptation of a mouse anti-human IL-13 antibody", Journal of Molecular Biology, vol. 398, pp. 214-231 (2010).
Brummell et al., "Probing the combining site of an anti-carbohydrate antibody by saturation-mutagenesis: role of the heavy-chain CDR3 residues", Biochemistry 21:1180-1187 (1993) (Abstract).
Kobayashi et al., "Tryptophan H33 plays an important role in pyrimidine (604) pyrimidone photoproduct binding by a high-affinity antibody", Protein Engineering 12:879-884 (1999).
Burks et al., "In Vitro scanning saturation mutagenesis of an antibody binding pocket" Proc. Natl Acad. Sci USA 94: 412-417 (1997).
Jang et al., "The structural basis for DNA binding by an anti-DNA autoantibody", Molecular Immunology, Immunol. 35:1207-1217 (1998).
Brorson et al., "Mutational Analysis of Avidity and Fine Specificity of Anti-Levan Antibodies", J. Immunol. 163:6694-6701 (1999).
Coleman, "Effects of amino acid sequence changes on antibody-antigen interatctions", Research in Immunology, 145:33-36 (1994).
Swanson, et al., International Search Report dated Jul. 6, 2012 that issued on the corresponding international patent application No. PCT/US09/53425.

* cited by examiner

Fig. 1

```
                    1                                                          60
SEQ ID  2 C863 LC  (1) DVQITQSPSYLAASPGETITLNCRASKSISKYLAWYQEKPGKTNKLLIYSGSTLQSGIPS
SEQ ID  9 VB L6    (1) EIVLTQSPATLSLSPGERATLSCRASKSISKYLAWYQQKPGQAPRLLIYSGSTLQSGIPA
SEQ ID  6 VB L18   (1) AIQLTQSPSSLSLSASVGDRVTITCRASKSISKYLAWYQQKPGKAPKLLIYSGSTLQSGVPS
SEQ ID  5 VB O12   (1) DIQMTQSPSSLSASVGDRVTITCRASKSISKYLAWYQQKPGKAPKLLIYSGSTLQSGVPS
SEQ ID 11 VB L12   (1) DIQMTQSPSTLSASVGDRVTITCRASKSISKYLAWYQQKPGKAPKLLIYSGSTLQSGVPS 61                                                         107
SEQ ID  2 C863 LC  (61) RFSGSGSGTDFTLTISSLEPEDFAMYFCQQHNEYPYTFGGGTKLEIK
SEQ ID  9 VB L6    (61) RFSGSGSGTDFTLTISSLEPEDFAVYYCQQHNEYPYTFGQGTKLEIK
SEQ ID  6 VB L18   (61) RFSGSGSGTDFTLTISSLQPEDFATYYCQQHNEYPYTFGQGTKVEIK
SEQ ID  5 VB O12   (61) RFSGSGSGTDFTLTISSLQPEDFATYYCQQHNEYPYTFGQGTKLEIK
SEQ ID 11 VB L12   (61) RFSGSGSGTEFTLTISSLQPDDFATYYCQQHNEYPYTFGQGTRLEIK 1                                                          60
SEQ ID  3 C863 HC  (1) QVTLKESGPGILQPSQTLSLTCSFSGFSLSTYGMGVGWIRQPSGKGLEWLAHIWWDDVKR
SEQ ID 20 VB 2-26  (1) QVTLKESGPVLVKPTETLTLTCTVSGFSLSTYGMGVGWIRQPPGKALEWLAHIWWDDVKR
SEQ ID 21 VB 2-05  (1) QITLKESGPTLVKPTQTLTLTCTFSGFSLSTYGMGVGWIRQPPGKALEWLAHIWWDDVKR 61                                                         121
SEQ ID  3 C863 HC  (61) YNPALKSRLTISKDTSGSQVFLKIASVDTSDTATYYCARMGSDYDVWFDYWGQGTLVTVSA
SEQ ID 20 VB 2-26  (61) YNPALKSRLTISKDTSKSQVVLTMTNMDPVDTATYYCARMGSDYDVWFDYWGQGTLVTVSS
SEQ ID 21 VB 2-05  (61) YNPALKSRLTITKDTSKNQVVLTMTNMDPVDTATYYCAHMGSDYDVWFDYWGQGTLVTVSS
```

Fig. 3A

Figure 3. Kabat's and Chothia's numbering systems and CDR's and HVL's definitions for representative antibodies.

Light Chain Sequences

| VL M1295 SEQ ID NO: 25 | VL-HFAL62 SEQ ID NO: 9 | VL-c836 SEQ ID NO: 2 | Sequential Numbering | Kabat | Chothia | CDR's (shaded) | HVL's (shaded) |
|---|---|---|---|---|---|---|---|
| E | E | D | 1 | 1 | 1 | | |
| I | I | V | 2 | 2 | 2 | | |
| V | V | Q | 3 | 3 | 3 | | |
| L | L | I | 4 | 4 | 4 | | |
| T | T | T | 5 | 5 | 5 | | |
| Q | Q | Q | 6 | 6 | 6 | | |
| S | S | S | 7 | 7 | 7 | | |
| P | P | P | 8 | 8 | 8 | | |
| A | A | S | 9 | 9 | 9 | | |
| T | T | Y | 10 | 10 | 10 | | |
| L | L | L | 11 | 11 | 11 | | |
| S | S | A | 12 | 12 | 12 | | |
| L | L | A | 13 | 13 | 13 | | |
| S | S | S | 14 | 14 | 14 | | |
| P | P | P | 15 | 15 | 15 | | |
| G | G | G | 16 | 16 | 16 | | |
| E | E | E | 17 | 17 | 17 | | |
| R | R | T | 18 | 18 | 18 | | |
| A | A | I | 19 | 19 | 19 | | |

Fig. 3B

| VL M1295 SEQ ID NO: 25 | VL-HFAL62 SEQ ID NO:9 | VL-c836 SEQ ID NO: 2 | Sequential Numbering | Kabat | Chothia | CDR's (shaded) | HVL's (shaded) |
|---|---|---|---|---|---|---|---|
| T | T | T | 20 | 20 | 20 | | |
| L | L | L | 21 | 21 | 21 | | |
| S | S | N | 22 | 22 | 22 | | |
| C | C | C | 23 | 23 | 23 | | |
| R | R | R | 24 | 24 | 24 | shaded | |
| A | A | A | 25 | 25 | 25 | shaded | |
| S | S | S | 26 | 26 | 26 | shaded | shaded |
| K | K | K | 27 | 27 | 27 | shaded | shaded |
| S | S | S | 28 | 28 | 28 | shaded | shaded |
| I | I | I | 29 | 29 | 29 | shaded | shaded |
| S | S | S | 30 | 30 | 30 | shaded | shaded |
| K | K | K | 31 | 31 | 31 | shaded | shaded |
| Y | Y | Y | 32 | 32 | 32 | shaded | shaded |
| L | L | L | 33 | 33 | 33 | shaded | |
| A | A | A | 34 | 34 | 34 | shaded | |
| W | W | W | 35 | 35 | 35 | shaded | |
| Y | Y | Y | 36 | 36 | 36 | shaded | |
| Q | Q | Q | 37 | 37 | 37 | shaded | |
| Q | Q | E | 38 | 38 | 38 | shaded | |
| K | K | K | 39 | 39 | 39 | shaded | |
| P | P | P | 40 | 40 | 40 | shaded | |
| G | G | G | 41 | 41 | 41 | | |
| Q | Q | K | 42 | 42 | 42 | | |
| A | A | T | 43 | 43 | 43 | | |
| P | P | N | 44 | 44 | 44 | | |

Fig. 3C

| VL M1295 SEQ ID NO: 25 | VL-HFAL62 SEQ ID NO:9 | VL-c836 SEQ ID NO: 2 | Sequential Numbering | Kabat | Chothia | CDR's (shaded) | HVL's (shaded) |
|---|---|---|---|---|---|---|---|
| R | R | K | 45 | 45 | 45 | | |
| L | L | L | 46 | 46 | 46 | | |
| L | L | L | 47 | 47 | 47 | | |
| I | I | I | 48 | 48 | 48 | | |
| Y | Y | Y | 49 | 49 | 49 | | |
| S | S | S | 50 | 50 | 50 | shaded | shaded |
| G | G | G | 51 | 51 | 51 | shaded | shaded |
| S | S | S | 52 | 52 | 52 | shaded | |
| T | T | T | 53 | 53 | 53 | shaded | |
| L | L | L | 54 | 54 | 54 | shaded | |
| Q | Q | Q | 55 | 55 | 55 | shaded | |
| S | S | S | 56 | 56 | 56 | shaded | |
| G | G | G | 57 | 57 | 57 | | |
| I | I | I | 58 | 58 | 58 | | |
| P | P | P | 59 | 59 | 59 | | |
| A | A | S | 60 | 60 | 60 | | |
| R | R | R | 61 | 61 | 61 | | |
| F | F | F | 62 | 62 | 62 | | |
| S | S | S | 63 | 63 | 63 | | |
| G | G | G | 64 | 64 | 64 | | |
| S | S | S | 65 | 65 | 65 | | |
| G | G | G | 66 | 66 | 66 | | |
| S | S | S | 67 | 67 | 67 | | |
| G | G | G | 68 | 68 | 68 | | |
| T | T | T | 69 | 69 | 69 | | |

Fig. 3D

| VL M1295 SEQ ID NO: 25 | VL-HFAL62 SEQ ID NO:9 | VL-c836 SEQ ID NO: 2 | Sequential Numbering | Kabat | Chothia | CDR's (shaded) | HVL's (shaded) |
|---|---|---|---|---|---|---|---|
| D | D | D | 70 | 70 | 70 | | |
| F | F | F | 71 | 71 | 71 | | |
| T | T | T | 72 | 72 | 72 | | |
| L | L | L | 73 | 73 | 73 | | |
| T | T | T | 74 | 74 | 74 | | |
| I | I | I | 75 | 75 | 75 | | |
| S | S | S | 76 | 76 | 76 | | |
| S | S | S | 77 | 77 | 77 | | |
| L | L | L | 78 | 78 | 78 | | |
| E | E | E | 79 | 79 | 79 | | |
| P | P | P | 80 | 80 | 80 | | |
| E | E | E | 81 | 81 | 81 | | |
| D | D | D | 82 | 82 | 82 | | |
| F | F | F | 83 | 83 | 83 | | |
| A | A | A | 84 | 84 | 84 | | |
| V | V | M | 85 | 85 | 85 | | |
| Y | Y | Y | 86 | 86 | 86 | | |
| Y | Y | F | 87 | 87 | 87 | | |
| C | C | C | 88 | 88 | 88 | | |
| Q | Q | Q | 89 | 89 | 89 | shaded | |
| Q | Q | Q | 90 | 90 | 90 | shaded | shaded |
| H | H | H | 91 | 91 | 91 | shaded | shaded |
| D | N | N | 92 | 92 | 92 | shaded | shaded |

Fig. 3E

| VL M1295 SEQ ID NO: 25 | VL-HFAL62 SEQ ID NO: 9 | VL-c836 SEQ ID NO: 2 | Sequential Numbering | Kabat | Chothia | CDR's (shaded) | HVL's (shaded) |
|---|---|---|---|---|---|---|---|
| —[1] | E | E | 93 | 93 | 93 | ▓▓ | ▓▓ |
| Y | Y | Y | 94 | 94 | 94 | ▓▓ | ▓▓ |
| P | P | P | 95 | 95 | 95 | ▓▓ | ▓▓ |
| Y | Y | Y | 96 | 96 | 96 | ▓▓ | |
| T | T | T | 97 | 97 | 97 | ▓▓ | |
| F | F | F | 98 | 98 | 98 | | |
| G | G | G | 99 | 99 | 99 | | |
| Q | Q | G | 100 | 100 | 100 | | |
| G | G | G | 101 | 101 | 101 | | |
| T | T | T | 102 | 102 | 102 | | |
| K | K | K | 103 | 103 | 103 | | |
| L | L | L | 104 | 104 | 104 | | |
| E | E | E | 105 | 105 | 105 | | |
| I | I | I | 106 | 106 | 106 | | |
| K | K | K | 107 | 107 | 107 | | |
| R | R | R | 108 | 108 | 108 | | |

[1] This position was deleted in the M1295 light chain. As such, the sequential numbering for M1295 is adjusted by one residue. For example the next residue (Tyr) is number 93 in M1295, but is number 94 in the VL-62 and c836 light chain sequences. This adjustment in numbering is reflected in the Sequence listing.

Fig. 3F

Heavy Chain Sequences

| VH-M1295 SEQ ID NO:26 | VH-62 SEQ ID NO:20 | VH-c836 SEQ ID NO: 3 | Sequential Numbering | Kabat | Chothia | Binding site (shaded) | |
|---|---|---|---|---|---|---|---|
| | | | | | | CDR's | HVL's |
| Q | Q | Q | 1 | 1 | 1 | | |
| V | V | V | 2 | 2 | 2 | | |
| T | T | T | 3 | 3 | 3 | | |
| L | L | L | 4 | 4 | 4 | | |
| K | K | K | 5 | 5 | 5 | | |
| E | E | E | 6 | 6 | 6 | | |
| S | S | S | 7 | 7 | 7 | | |
| G | G | G | 8 | 8 | 8 | | |
| P | P | P | 9 | 9 | 9 | | |
| V | V | G | 10 | 10 | 10 | | |
| L | L | I | 11 | 11 | 11 | | |
| V | V | L | 12 | 12 | 12 | | |
| K | K | Q | 13 | 13 | 13 | | |
| P | P | P | 14 | 14 | 14 | | |
| T | T | S | 15 | 15 | 15 | | |
| E | E | Q | 16 | 16 | 16 | | |
| T | T | T | 17 | 17 | 17 | | |
| L | L | L | 18 | 18 | 18 | | |
| T | T | S | 19 | 19 | 19 | | |
| L | L | L | 20 | 20 | 20 | | |
| T | T | T | 21 | 21 | 21 | | |
| C | C | C | 22 | 22 | 22 | | |
| T | T | S | 23 | 23 | 23 | | |
| V | V | F | 24 | 24 | 24 | | |

Fig. 3G

| VH-M1295 SEQ ID NO:26 | VH-62 SEQ ID NO:20 | VH-c836 SEQ ID NO:3 | Sequential Numbering | Kabat | Chothia | Binding site (shaded) CDR's | HVL's |
|---|---|---|---|---|---|---|---|
| S | S | S | 25 | 25 | 25 | | ▓ |
| G | G | G | 26 | 26 | 26 | | ▓ |
| F | F | F | 27 | 27 | 27 | | ▓ |
| S | S | S | 28 | 28 | 28 | | ▓ |
| L | L | L | 29 | 29 | 29 | | ▓ |
| S | S | S | 30 | 30 | 30 | | ▓ |
| T | T | T | 31 | 31 | 31 | | ▓ |
| Y | Y | Y | 32 | 32 | a | | ▓ |
| G | G | G | 33 | 33 | b | | |
| V | M | M | 34 | 34 | 32 | | |
| G | G | G | 35 | 35 | 33 | ▓ | |
| V | V | V | 36 | a | 34 | ▓ | |
| G | G | G | 37 | b | 35 | ▓ | |
| W | W | W | 38 | 36 | 36 | ▓ | |
| I | I | I | 39 | 37 | 37 | ▓ | |
| R | R | R | 40 | 38 | 38 | | |
| Q | Q | Q | 41 | 39 | 39 | | |
| P | P | P | 42 | 40 | 40 | | |
| P | P | S | 43 | 41 | 41 | | |
| G | G | G | 44 | 42 | 42 | | |
| K | K | K | 45 | 43 | 43 | | |
| A | A | G | 46 | 44 | 44 | | |
| L | L | L | 47 | 45 | 45 | | |
| E | E | E | 48 | 46 | 46 | | |
| W | W | W | 49 | 47 | 47 | | |

Fig. 3H

| VH-M1295 SEQ ID NO:26 | VH-62 SEQ ID NO:20 | VH-c836 SEQ ID NO:3 | Sequential Numbering | Kabat | Chothia | Binding site (shaded) CDR's | HVL's |
|---|---|---|---|---|---|---|---|
| L | L | L | 50 | 48 | 48 | | |
| A | A | A | 51 | 49 | 49 | | |
| H | H | H | 52 | 50 | 50 | ▓ | |
| I | I | I | 53 | 51 | 51 | ▓ | |
| W | W | W | 54 | 52 | 52 | ▓ | ▓ |
| W | W | W | 55 | 53 | 53 | ▓ | ▓ |
| D | D | D | 56 | 54 | 54 | ▓ | ▓ |
| D | D | D | 57 | 55 | 55 | ▓ | ▓ |
| V | V | V | 58 | 56 | 56 | ▓ | ▓ |
| K | K | K | 59 | 57 | 57 | ▓ | |
| R | R | R | 60 | 58 | 58 | ▓ | |
| Y | Y | Y | 61 | 59 | 59 | ▓ | |
| N | N | N | 62 | 60 | 60 | ▓ | |
| P | P | P | 63 | 61 | 61 | ▓ | |
| A | A | A | 64 | 62 | 62 | ▓ | |
| L | L | L | 65 | 63 | 63 | ▓ | |
| K | K | K | 66 | 64 | 64 | ▓ | |
| S | S | S | 67 | 65 | 65 | ▓ | |
| R | R | R | 68 | 66 | 66 | | |
| L | L | L | 69 | 67 | 67 | | |
| T | T | T | 70 | 68 | 68 | | |
| I | I | I | 71 | 69 | 69 | | |
| S | S | S | 72 | 70 | 70 | | |
| K | K | K | 73 | 71 | 71 | | |
| D | D | D | 74 | 72 | 72 | | |

Fig. 3I

| VH-M1295 SEQ ID NO:26 | VH-62 SEQ ID NO:20 | VH-c836 SEQ ID NO:3 | Sequential Numbering | Kabat | Chothia | Binding site (shaded) CDR's | HVL's |
|---|---|---|---|---|---|---|---|
| T | T | T | 75 | 73 | 73 | | |
| S | S | S | 76 | 74 | 74 | | |
| K | K | G | 77 | 75 | 75 | | |
| S | S | S | 78 | 76 | 76 | | |
| Q | Q | Q | 79 | 77 | 77 | | |
| V | V | V | 80 | 78 | 78 | | |
| V | V | F | 81 | 79 | 79 | | |
| L | L | L | 82 | 80 | 80 | | |
| T | T | K | 83 | 81 | 81 | | |
| M | M | I | 84 | 82 | 82 | | |
| T | T | A | 85 | a | a | | |
| N | N | S | 86 | b | b | | |
| M | M | V | 87 | c | c | | |
| D | D | D | 88 | 83 | 83 | | |
| P | P | T | 89 | 84 | 84 | | |
| V | V | S | 90 | 85 | 85 | | |
| D | D | D | 91 | 86 | 86 | | |
| T | T | T | 92 | 87 | 87 | | |
| A | A | A | 93 | 88 | 88 | | |
| T | T | T | 94 | 89 | 89 | | |
| Y | Y | Y | 95 | 90 | 90 | | |
| Y | Y | Y | 96 | 91 | 91 | | |
| C | C | C | 97 | 92 | 92 | | |
| A | A | A | 98 | 93 | 93 | | |
| R | R | R | 99 | 94 | 94 | | |

Fig. 3J

| VH-M1295 SEQ ID NO:26 | VH-62 SEQ ID NO:20 | VH-c836 SEQ ID NO: 3 | Sequential Numbering | Kabat | Chothia | Binding site (shaded) CDR's | HVL's |
|---|---|---|---|---|---|---|---|
| L | M | M | 100 | 95 | 95 | ▨ | ▨ |
| G | G | G | 101 | 96 | 96 | ▨ | ▨ |
| S | S | S | 102 | 97 | 97 | ▨ | ▨ |
| D | D | D | 103 | 98 | 98 | ▨ | ▨ |
| Y | Y | Y | 104 | 99 | 99 | ▨ | ▨ |
| D | D | D | 105 | 100 | 100 | ▨ | ▨ |
| V | V | V | 106 | a | a | ▨ | ▨ |
| W | W | W | 107 | b | b | ▨ | ▨ |
| F | F | F | 108 | c | c | ▨ | ▨ |
| D | D | D | 109 | 101 | 101 | ▨ | ▨ |
| Y | Y | Y | 110 | 102 | 102 | ▨ | ▨ |
| W | W | W | 111 | 103 | 103 | | |
| G | G | G | 112 | 104 | 104 | | |
| Q | Q | Q | 113 | 105 | 105 | | |
| G | G | G | 114 | 106 | 106 | | |
| T | T | T | 115 | 107 | 107 | | |
| L | L | L | 116 | 108 | 108 | | |
| V | V | V | 117 | 109 | 109 | | |
| T | T | T | 118 | 110 | 110 | | |
| V | V | V | 119 | 111 | 111 | | |
| S | S | S | 120 | 112 | 112 | | |
| A | A | A | 121 | 113 | 113 | | |
| S | S | S | 122 | 114 | 114 | | |

SEQUENCE LISTING

```
<160> NUMBER OF SEQ ID NOS: 29

<210> SEQ ID NO 1
<211> LENGTH: 112
<212> TYPE: PRT
<213> ORGANISM: Homo sapiens
<220> FEATURE:
<221> NAME/KEY: VARIANT
<222> LOCATION: (110)..(110)
<223> OTHER INFORMATION: Residue may be R or Q

<400> SEQUENCE: 1

Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Xaa Phe Asn
            100                 105                 110

<210> SEQ ID NO 2
<211> LENGTH: 107
<212> TYPE: PRT
<213> ORGANISM: Mus musculus
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 2

Asp Val Gln Ile Thr Gln Ser Pro Ser Tyr Leu Ala Ala Ser Pro Gly
1               5                   10                  15

Glu Thr Ile Thr Leu Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Met Tyr Phe Cys Gln Gln His Asn Glu Tyr Pro Tyr
                 85                  90                  95

Thr Phe Gly Gly Gly Thr Lys Leu Glu Ile Lys
            100                 105
```

<210> SEQ ID NO 3
<211> LENGTH: 121
<212> TYPE: PRT
<213> ORGANISM: Mus musculus
<220> FEATURE:
<221> NAME/KEY: BINDING
<222> LOCATION: (26)..(37)
<223> OTHER INFORMATION: CDR1
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(110)
<223> OTHER INFORMATION: CDR3

<400> SEQUENCE: 3

```
Gln Val Thr Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Ser Thr Tyr
                 20                  25                  30

Gly Met Gly Val Gly Trp Ile Arg Gln Pro Ser Gly Lys Gly Leu Glu
             35                  40                  45

Trp Leu Ala His Ile Trp Trp Asp Asp Val Lys Arg Tyr Asn Pro Ala
 50                  55                  60

Leu Lys Ser Arg Leu Thr Ile Ser Lys Asp Thr Ser Gly Ser Gln Val
 65                  70                  75                  80

Phe Leu Lys Ile Ala Ser Val Asp Thr Ser Asp Thr Ala Thr Tyr Tyr
                 85                  90                  95

Cys Ala Arg Met Gly Ser Asp Tyr Asp Val Trp Phe Asp Tyr Trp Gly
             100                 105                 110

Gln Gly Thr Leu Val Thr Val Ser Ala
            115                 120
```

<210> SEQ ID NO 4
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 4

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Lys Ser Ile Ser Lys Tyr
```

```
                    20                  25                  30

Leu Ala Trp Tyr Gln Gln Lys Pro Gly Lys Val Pro Lys Leu Leu Ile
            35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 5
<211> LENGTH: 107
<212> TYPE: PRT
<213> ORGANISM: Artificial sequence
<220> FEATURE:
<223> OTHER INFORMATION: Human framework adapted murine immunoglobulin
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
            35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gln Gly Thr Lys Leu Glu Ile Lys
            100                 105

<210> SEQ ID NO 6
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
```

<223> OTHER INFORMATION: CDR3

<400> SEQUENCE: 6

Ala Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 7
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Arg Leu Ile
        35                  40                  45

Tyr Ser Gly Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Human framework adapted murine light chain
      variable region
<220> FEATURE:
<221> NAME/KEY: BINDING
<222> LOCATION: (24)..(34)

```
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 8

Asp Ile Gln Leu Thr Gln Ser Pro Ser Phe Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gln Gly Thr Lys Val Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Asn Glu Tyr Pro Tyr
                85                  90                  95

Thr Phe Gly Gln Gly Thr Lys Leu Glu Ile Lys
            100                 105

<210> SEQ ID NO 10
<211> LENGTH: 107
```

```
<212> TYPE: PRT
<213> ORGANISM: Artificial Sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 10

Asp Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Arg Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Gln His Asn Glu Tyr Pro Tyr
                85                  90                  95

Thr Phe Gly Gln Gly Thr Lys Leu Glu Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln His Asn Glu Tyr Pro Tyr
```

```
                    85                  90                  95
Thr Phe Gly Gln Gly Thr Arg Leu Glu Ile Lys
            100                 105

<210> SEQ ID NO 12
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Ala Pro Lys Ser Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 13
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 13

Asp Ile Gln Leu Thr Gln Ser Pro Ser Phe Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45
```

```
Tyr Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 14
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 14

Ala Ile Arg Met Thr Gln Ser Pro Ser Ser Phe Ser Ala Ser Thr Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 15
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Glu Lys Ala Pro Lys Ser Leu Ile
        35                  40                  45

Tyr Ser Gly Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
                100                 105
```

<210> SEQ ID NO 16
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 16

```
Asn Ile Gln Met Thr Gln Ser Pro Ser Ala Met Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Phe Gln Gln Lys Pro Gly Lys Val Pro Lys His Leu Ile
        35                  40                  45

Tyr Ser Gly Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
                100                 105
```

<210> SEQ ID NO 17
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)

```
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 17

Asp Ile Gln Met Thr Gln Ser Pro Ser Thr Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 18
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 18

Val Ile Trp Met Thr Gln Ser Pro Ser Leu Leu Ser Ala Ser Thr Gly
1               5                   10                  15

Asp Arg Val Thr Ile Ser Cys Arg Ala Ser Lys Ser Ile Ser Lys Tyr
            20                  25                  30

Leu Ala Trp Tyr Gln Gln Lys Pro Gly Lys Ala Pro Glu Leu Leu Ile
        35                  40                  45

Tyr Ser Gly Ser Thr Leu Gln Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 19
<211> LENGTH: 121
<212> TYPE: PRT
<213> ORGANISM: Artificial sequence
<220> FEATURE:
<223> OTHER INFORMATION: Human framework adapted murine heavy chain
``` variable region
<220> FEATURE:
<221> NAME/KEY: BINDING
<222> LOCATION: (26)..(37)
<223> OTHER INFORMATION: CDR1
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(110)
<223> OTHER INFORMATION: CDR3

<400> SEQUENCE: 19

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Gly Ser Asp Tyr Asp Val Trp Phe Asp Tyr Trp Gly
            100                 105                 110

Gln Gly Thr Leu Val Thr Val Ser Ser
        115                 120

<210> SEQ ID NO 20
<211> LENGTH: 121
<212> TYPE: PRT
<213> ORGANISM: Artificial sequence
<220> FEATURE:
<223> OTHER INFORMATION: Human framework adapted murine heavy chain
      variable region
<220> FEATURE:
<221> NAME/KEY: BINDING
<222> LOCATION: (26)..(37)
<223> OTHER INFORMATION: CDR1
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(110)
<223> OTHER INFORMATION: CDR3

<400> SEQUENCE: 20

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

```
Cys Ala Arg Met Gly Ser Asp Tyr Asp Val Trp Phe Asp Tyr Trp Gly
            100                 105                 110

Gln Gly Thr Leu Val Thr Val Ser Ser
        115                 120

<210> SEQ ID NO 21
<211> LENGTH: 121
<212> TYPE: PRT
<213> ORGANISM: Artificial sequence
<220> FEATURE:
<223> OTHER INFORMATION: Human framework adapted murine heavy chain
      variable region
<220> FEATURE:
<221> NAME/KEY: BINDING
<222> LOCATION: (26)..(37)
<223> OTHER INFORMATION: CDR1
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(110)
<223> OTHER INFORMATION: CDR3

<400> SEQUENCE: 21

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Met Gly Ser Asp Tyr Asp Val Trp Phe Asp Tyr Trp Gly
            100                 105                 110

Gln Gly Thr Leu Val Thr Val Ser Ser
        115                 120

<210> SEQ ID NO 22
<211> LENGTH: 121
<212> TYPE: PRT
<213> ORGANISM: Artificial sequence
<220> FEATURE:
<223> OTHER INFORMATION: Human framework adapted murine heavy chain
      variable region
<220> FEATURE:
<221> NAME/KEY: BINDING
<222> LOCATION: (26)..(37)
<223> OTHER INFORMATION: CDR1
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(110)
<223> OTHER INFORMATION: CDR3

<400> SEQUENCE: 22

Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Phe Ser Leu Ser Thr Tyr
            20                  25                  30

Gly Met Gly Val Gly Trp Ile Arg Gln Pro Pro Gly Lys Gly Leu Glu
            35                  40                  45

Trp Ile Gly His Ile Trp Trp Asp Asp Val Lys Arg Tyr Asn Pro Ala
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
            85                  90                  95

Cys Ala Arg Met Gly Ser Asp Tyr Asp Val Trp Phe Asp Tyr Trp Gly
            100                 105                 110

Gln Gly Thr Leu Val Thr Val Ser Ser
            115                 120

<210> SEQ ID NO 23
<211> LENGTH: 121
<212> TYPE: PRT
<213> ORGANISM: Artificial sequence
<220> FEATURE:
<223> OTHER INFORMATION: Human framework adapted murine heavy chain
      variable region
<220> FEATURE:
<221> NAME/KEY: BINDING
<222> LOCATION: (26)..(37)
<223> OTHER INFORMATION: CDR1
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(110)
<223> OTHER INFORMATION: CDR3

<400> SEQUENCE: 23

Gln Val Gln Leu Gln Glu Ser Gly Pro Gly Leu Val Lys Pro Ser Asp
 1               5                   10                  15

Thr Leu Ser Leu Thr Cys Ala Val Ser Gly Phe Ser Leu Ser Thr Tyr
            20                  25                  30

Gly Met Gly Val Gly Trp Ile Arg Gln Pro Pro Gly Lys Gly Leu Glu
            35                  40                  45

Trp Ile Gly His Ile Trp Trp Asp Asp Val Lys Arg Tyr Asn Pro Ala
 50                  55                  60

Leu Lys Ser Arg Val Thr Met Ser Val Asp Thr Ser Lys Asn Gln Phe
 65                  70                  75                  80

Ser Leu Lys Leu Ser Ser Val Thr Ala Val Asp Thr Ala Val Tyr Tyr
            85                  90                  95

Cys Ala Arg Met Gly Ser Asp Tyr Asp Val Trp Phe Asp Tyr Trp Gly
            100                 105                 110

Gln Gly Thr Leu Val Thr Val Ser Ser
            115                 120

<210> SEQ ID NO 24
<211> LENGTH: 121
<212> TYPE: PRT
<213> ORGANISM: Artificial sequence
<220> FEATURE:
<223> OTHER INFORMATION: Human framework adapted murine heavy chain
      variable region
<220> FEATURE:
<221> NAME/KEY: BINDING
<222> LOCATION: (26)..(37)
<223> OTHER INFORMATION: CDR1
```

```
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(110)
<223> OTHER INFORMATION: CDR3

<400> SEQUENCE: 24
```

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Leu Ser Thr Tyr
            20                  25                  30

Gly Met Gly Val Gly Trp Val Arg Gln Ala Pro Gly Lys Gly Leu Glu
        35                  40                  45

Trp Val Ala His Ile Trp Trp Asp Asp Val Lys Arg Tyr Asn Pro Ala
    50                  55                  60

Leu Lys Ser Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Met Gly Ser Asp Tyr Asp Val Trp Phe Asp Tyr Trp Gly
            100                 105                 110

Gln Gly Thr Leu Val Thr Val Ser Ser
        115                 120

```
<210> SEQ ID NO 25
<211> LENGTH: 106
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: BINDING
<222> LOCATION: (24)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(97)
<223> OTHER INFORMATION: CDR3

<400> SEQUENCE: 25
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Asp Tyr Pro Tyr Thr
                85                  90                  95

Phe Gly Gln Gly Thr Lys Leu Glu Ile Lys
            100                 105

```
<210> SEQ ID NO 26
<211> LENGTH: 121
<212> TYPE: PRT
<213> ORGANISM: Artificial sequence
<220> FEATURE:
<223> OTHER INFORMATION: Human framework adapted murine heavy chain
      variable region
<220> FEATURE:
<221> NAME/KEY: BINDING
<222> LOCATION: (26)..(37)
<223> OTHER INFORMATION: CDR1
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(110)
<223> OTHER INFORMATION: CDR3

<400> SEQUENCE: 26

Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Thr Tyr
             20                  25                  30

Gly Val Gly Val Gly Trp Ile Arg Gln Pro Pro Gly Lys Ala Leu Glu
         35                  40                  45

Trp Leu Ala His Ile Trp Trp Asp Asp Val Lys Arg Tyr Asn Pro Ala
 50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Leu Gly Ser Asp Tyr Asp Val Trp Phe Asp Tyr Trp Gly
            100                 105                 110

Gln Gly Thr Leu Val Thr Val Ser Ser
        115                 120

<210> SEQ ID NO 27
<211> LENGTH: 107
<212> TYPE: PRT
<213> ORGANISM: Artificial sequence
<220> FEATURE:
<223> OTHER INFORMATION: Human framework adapted murine light chain
      variable region
<220> FEATURE:
<221> NAME/KEY: VARIANT
<222> LOCATION: (38)..(38)
<223> OTHER INFORMATION: X may be Met, Ser, Leu, Glu, Gln, or Val
<220> FEATURE:
<221> NAME/KEY: VARIANT
<222> LOCATION: (54)..(54)
<223> OTHER INFORMATION: X may be Leu or Gln
<220> FEATURE:
<221> NAME/KEY: VARIANT
<222> LOCATION: (91)..(91)
<223> OTHER INFORMATION: X may be His, Gln, or Pro
<220> FEATURE:
<221> NAME/KEY: VARIANT
<222> LOCATION: (92)..(92)
<223> OTHER INFORMATION: X may be Asn, Asp, Ser, Leu, Pro, Ile, Phe,
      Glu, or Val
<220> FEATURE:
<221> NAME/KEY: VARIANT
<222> LOCATION: (93)..(93)
<223> OTHER INFORMATION: X may be Glu, Asp, Gly, Ser, Ile, Tyr, Trp,
      Asn, His, Val, Met, Arg, Leu, Phe, Pro or absent
<220> FEATURE:
<221> NAME/KEY: VARIANT
<222> LOCATION: (94)..(94)
<223> OTHER INFORMATION: X may be Tyr, Gly, Ser, Ala, Val, Phe, Thr,
```

-continued

Glu, or be absent

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Ile Ser Lys Tyr
            20                  25                  30

Leu Ala Trp Tyr Gln Xaa Lys Pro Gly Gln Ala Pro Arg Leu Leu Ile
        35                  40                  45

Tyr Ser Gly Ser Thr Xaa Gln Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Xaa Xaa Xaa Xaa Pro Tyr
                85                  90                  95

Thr Phe Gly Gln Gly Thr Lys Leu Glu Ile Lys
            100                 105

<210> SEQ ID NO 28
<211> LENGTH: 121
<212> TYPE: PRT
<213> ORGANISM: Artificial sequence
<220> FEATURE:
<223> OTHER INFORMATION: Human framework adapted murine heavy chain
      variable region
<220> FEATURE:
<221> NAME/KEY: VARIANT
<222> LOCATION: (31)..(31)
<223> OTHER INFORMATION: X may be Thr or Ser
<220> FEATURE:
<221> NAME/KEY: VARIANT
<222> LOCATION: (34)..(34)
<223> OTHER INFORMATION: X may be Met, Ser, Leu, Glu, Gln, or Val
<220> FEATURE:
<221> NAME/KEY: VARIANT
<222> LOCATION: (100)..(100)
<223> OTHER INFORMATION: X may be Met or Leu
<220> FEATURE:
<221> NAME/KEY: VARIANT
<222> LOCATION: (106)..(106)
<223> OTHER INFORMATION: X may be Val or Ile

<400> SEQUENCE: 28

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Xaa Tyr
            20                  25                  30

Gly Xaa Gly Val Gly Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Xaa Gly Ser Asp Tyr Asp Xaa Trp Phe Asp Tyr Trp Gly
            100                 105                 110

Gln Gly Thr Leu Val Thr Val Ser Ser
        115                 120

<210> SEQ ID NO 29
<211> LENGTH: 9
<212> TYPE: PRT

```
<213> ORGANISM: Artificial sequence
<220> FEATURE:
<223> OTHER INFORMATION: Active variants of murine CDR3
<220> FEATURE:
<221> NAME/KEY: VARIANT
<222> LOCATION: (3)..(3)
<223> OTHER INFORMATION: Xaa may be His, Gln, or Pro
<220> FEATURE:
<221> NAME/KEY: VARIANT
<222> LOCATION: (4)..(4)
<223> OTHER INFORMATION: Xaa may be Asn, Asp, Ser, Leu, Pro, Ile, Phe,
      Glu, or Val
<220> FEATURE:
<221> NAME/KEY: VARIANT
<222> LOCATION: (5)..(5)
<223> OTHER INFORMATION: Xaa may be  Glu, Asp, Gly, Ser, Ile, Tyr, Trp,
      Asn, His, Val, Met, Arg, Leu, Phe, Pro or be absent
<220> FEATURE:
<221> NAME/KEY: VARIANT
<222> LOCATION: (6)..(6)
<223> OTHER INFORMATION: Xaa may be  Tyr, Gly, Ser, Ala, Val, Phe, Thr,
      Glu or be absent

<400> SEQUENCE: 29

Gln Gln Xaa Xaa Xaa Xaa Pro Tyr Thr
1               5
```

ENGINEERED ANTI-IL-13 ANTIBODIES, COMPOSITIONS, METHODS AND USES

CROSS-REFERENCE TO RELATED APPLICATIONS

This application is a 35 USC §371 national stage entry of, and claims priority to, International Application Number PCT/US2009/053425, filed 11 Aug. 2009, which claims priority to: U.S. Provisional Application No. 61/090,472 filed 20 Aug. 2008; and U.S. Provisional Application No. 61/097,232, filed 16 Sep. 2008. The entire contents of each of the aforesaid applications are incorporated herein by reference in their entirety.

FIELD OF THE INVENTION

The present invention relates to engineered antibodies immunospecific for human interleukin-13 (IL-13) protein or fragment thereof, as well as methods of making and using thereof, including therapeutic indications.

BACKGROUND

IL-13 is a globular protein containing four α-helices belonging to the family of growth hormone-like cytokines which includes IL-4, granulocyte macrophage-colony-stimulating factor, IL-2, and macrophage-colony-stimulating factor. IL-13 binds to a heterodimeric receptor composed of IL-13Rα1, a 52-kDa subunit, and p140, a 140 kDa subunit, resulting in activation of STATE. A second IL-13 receptor, Ra2, is also known to exist. The Ra1 receptor is responsible for initiating the signaling cascade upon binding with IL-13. The Ra2 receptor binds to IL-13 with greater affinity than Ra1 however its function has yet to be determined.

Patients experiencing an asthmatic response have an increase of activated CD4+Th2 lymphocytes that cause inflammation of the airways. Activated Th2 lymphocytes secrete cytokines (IL-4, IL-5, IL-9, IL-10 and IL-13) that stimulate inflammation causing tissue damage associated with airway hyper-reactivity. IL-13 has been shown to be a major contributing factor of asthma in murine models and the human IL-13 variant of a single nucleotide polymorphism, R130Q (Graves, et al., 2000 J Allergy Clin Immunol 105: 506-13) was shown to be a significant risk factor for asthma development (Heinzmann et al., 2000 Hum. Mol. Genet. 9:549-559; Am. J. Respir.; Howard et al., 2001 Cell Mol. Biol. 25:377-384; WO0123410). Treatment with an anti-IL-13 neutralizing Mab in a murine model inhibited an asthmatic response in stimulated animals. Thus, evidence indicates that neutralizing IL-13 could be beneficial in treating asthma and airway constriction in patients.

Accordingly, there is a need to provide human antibodies specific for human IL-13 for use in therapy to diminish or eliminate IL-13-mediated diseases, as well as improvements over known antibodies or fragments thereof.

SUMMARY OF THE INVENTION

The subject matter described and claimed herein relates to anti-IL-13 antibodies and compositions useful to treat subjects suffering from pathologies or conditions associated with IL-13 including, but not limited to, respiratory conditions such as asthma and pulmonary fibrosis, cardiovascular conditions, cancer, dermatological, and fibrotic conditions. The present invention provides anti-IL-13 monoclonal antibodies capable of blocking the biological activity of IL-13, in vitro, in vivo, or in situ including, but not limited to, inhibiting wild-type or natural variants of human IL-13 binding to the human IL-13 receptor alpha 1, inhibiting human IL-13 or natural variants of human IL-13 binding to the human IL-13 receptor alpha 2, preventing or suppressing human IL-13-dependent proliferation of human tumor cells, inhibiting human IL-13-dependent IgE production, reducing eosinophilic infiltration of tissues, and which antibody has a specific binding site on human IL-13. Amino acid sequences of exemplary anti-IL-13 monoclonal antibodies are provided which can be encoded by nucleic acids for expression in a host cell.

Antibodies or antibody fragments with binding domains constructed from selected binding fragments and as specified variants comprising the amino acid sequences in SEQ ID NOs: 27 and 28 are included within the scope of the present invention. The invention provides specified compositions and teachings for preparation of such compositions comprising residues involved in antigen binding in an immunoglobulin variable domain selected from SEQ ID NOs: 2-29. These binding domains have the desired characteristics and can modulate the biological activity needed to treat a particular IL-13-related pathology. In one aspect, the invention is an isolated antibody comprising the heavy chain variable region of SEQ ID NO: 28 and a light chain CDR3 (L-CDR3) according to Formula (I):

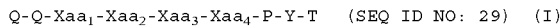

Q-Q-Xaa$_1$-Xaa$_2$-Xaa$_3$-Xaa$_4$-P-Y-T    (SEQ ID NO: 29)    (I)

where Xaa$_1$ may be His, Gln, or Pro;
Xaa$_2$ may be Asn, Asp, Ser, Leu, Pro, Ile, Phe, Glu, or Val;
Xaa$_3$ may be Glu, Asp, Gly, Ser, Ile, Tyr, Tryp, Asn, His, Val, Met, Arg, Leu, Phe, Pro or be absent; and
Xaa$_4$ may be Tyr, Gly, Ser, Ala, Val, Phe, Thr, Glu, or be absent.

In a particular embodiment, the antibody comprises the binding domains of SEQ ID NO: 25 and 26.

In another aspect, the invention relates to an antibody which binds to a common epitope on human wild-type IL-13 (SEQ ID NO:1) that is defined by the binding of an engineered anti-IL-13 antibody M1295 comprising SEQ ID NOs: 25 and 26, and a murine-human chimeric antibody designated C863 (comprising SEQ ID NOs: 2 and 3). The epitope recognized by these antibodies includes 8 residues of IL-13, three from helix A (Arg10, Ile13, Glu14) and 5 residues from helix D (Leu100, Lys103, Phe106, Arg107, Glu108), where the interatomic distances do not exceed 4.0 Å. Based on the number of contacts, Arg10 and Arg107 appear to be key residues of the epitope.

In a further embodiment, there are provided antigen epitopes as a component of a vaccine. The epitope described above comprising residues 10, 13, 14, 100, 103, and 106-108 of SEQ ID NO: 1 are recognized by antibodies of the invention, are useful for actively immunizing a host to elicit production of antibodies against IL-13. The antibodies produced are capable of treating or preventing pathological conditions associated with IL-13 bioactivity.

Another embodiment relates to the treatment or prevention of pathological conditions associated with IL-13 biological activity by administering a therapeutically or prophylactically effective amount of an antibody, or combination of antibodies, of the present invention to a subject in need of such treatment. In one aspect, an anti-IL-13 antibody is administered to a patient diagnosed with asthma. In another aspect, an anti-IL-13 antibody is administered to a patient diagnosed with atopic dermatitis.

The present invention provides, in one aspect, isolated nucleic acid molecules encoding a sequence, domain, portion, or variant of an anti-IL-13 antibody as described herein. Further contemplated are nucleic acid sequences that hybridize or complement the nucleic acid sequences encoding an anti-IL-13 antibody. The present invention further provides recombinant vectors comprising said anti-IL-13 antibody nucleic acid molecules, host cells containing such nucleic acids and/or recombinant vectors, as well as methods of making and/or using such antibody nucleic acids, vectors and/or host cells. The invention also provides that the encoded sequence, domain, portion or variant of the present IL-13 binding antibody may be administered to a patient in a composition comprising a suitable carrier solution or agent, as a pharmaceutically acceptable composition.

The invention also relates to methods of generating, purifying, and packaging an antibody described herein for use in the treatment or prevention of pathological conditions associated with IL-13 bioactivity by administering a therapeutically or prophylactically effective amount of an antibody. The present invention provides a method for expressing an anti-IL-13 antibody in a host cell, comprising culturing a host cell as described herein under conditions wherein an anti-IL-13 antibody is expressed in detectable and recoverable amounts.

In sum, the subject matter disclosed and claimed herein includes:

An isolated monoclonal antibody or antigen binding fragment thereof that binds to an epitope of IL-13 (SEQ ID NO:1) wherein said epitope comprises a position 10 arginine and a position 107 arginine of SEQ ID NO: 1; and may further comprise a residue selected from the group consisting of: a position 6 serine, a position 13 isoleucine, a position 14 glutamic acid, a position 100 leucine, a position 103 lysine, a position 106 phenylalanine, and a position 108 glutamic acid of SEQ ID NO:1;

An isolated monoclonal antibody or antigen binding fragment thereof comprising a paratope comprising a light chain variable region and further comprising a tyrosine residue that a) interacts with IL-13 at the position 10 arginine; and b) forms a bond with a position 14 glutamic acid of SEQ ID NO:1. The paratope may further comprise a histidine residue and asparagine residue on said light chain variable region, and may further comprise a heavy chain variable region comprising paratope contact residues selected from the group consisting of tyrosine, tryptophan, aspartic acid, valine, and arginine. The light chain variable region of the paratope may comprise SEQ ID NO: 2 and said tyrosine is at position 32 of SEQ ID NO: 2, and said heavy chain variable region comprises SEQ ID NO:3 and said contact residues comprise a position 32 tyrosine, a position 54 tryptophan, and a position 104 tyrosine;

An isolated monoclonal antibody or antigen binding fragment thereof comprising a paratope comprising a light chain variable region and further comprising an aspartic acid residue that a) interacts with IL-13 at the position 10 arginine; and b) forms a bond with a position 6 serine of SEQ ID NO:1, wherein said paratope further comprises a tyrosine residue and a histidine residue on said light chain variable region. The paratope may further comprise a heavy chain variable region comprising paratope contact residues selected from the group consisting of tyrosine, tryptophan, aspartic acid, valine, and arginine. The light chain variable region may comprise SEQ ID NO: 25 and said aspartic acid is at position 92 of SEQ ID NO: 25, and the heavy chain variable region may comprise SEQ ID NO:26 and said contact residues comprise a position 32 tyrosine, a position 54 tryptophan, and a position 104 tyrosine;

An isolated monoclonal antibody or antigen-binding fragment thereof that competes for binding to an epitope of IL-13 with a monoclonal antibody selected from the group consisting of C863, HFAL62, and M1295. The monoclonal antibody comprises a light chain CDR3 (L-CDR3) of SEQ ID NO:29 and L-CDR3 of SEQ ID NO: 29 is further defined as shown in Formula (I): Formula (I)-Q-Q-Xaa$_1$-Xaa$_2$-Xaa$_3$-Xaa$_4$-P-Y-T (SEQ ID NO: 29) wherein Xaa$_1$ may be His, Gln, or Pro; Xaa$_2$ may be Asn, Asp, Ser, Leu, Pro, Ile, Phe, Glu, or Val; Xaa$_3$ may be Glu, Asp, Gly, Ser, Ile, Tyr, Tryp, Asn, His, Val, Met, Arg, Leu, Phe, Pro or be absent; and Xaa$_4$ may be Tyr, Gly, Ser, Ala, Val, Phe, Thr, Glu, or be absent. The monoclonal antibody may comprise the heavy chain variable region of SEQ ID NO: 28 and/or the light chain variable region of SEQ ID NO: 27;

An isolated monoclonal antibody comprising the variable light chain of SEQ ID NO: 9 and variants thereof, and the variable heavy chain of SEQ ID NO: 20, and variants thereof. The variants of the variable light chain of SEQ ID NO: 9 comprise changes at the residues selected from the group consisting of a position 91 histidine, a position 92 asparagine, a position 93 glutamic acid, and a position 94 tyrosine. The variants of the variable heavy chain of SEQ ID NO: 20 comprise changes at the residues selected from the group consisting of a position 31 threonine, a position 34 methionine, a position 100 methionine, and a position 106 valine.

An isolated monoclonal antibody, or antigen binding fragment thereof, comprising the light chain variable region of SEQ ID NO: 25, and the heavy chain variable region of SEQ ID NO: 26. The antibody further comprises corresponding light and heavy chain immunoglobulin constant regions and a heavy chain hinge region. The antibody, as well as any other antibody described herein, may be prepared in a pharmaceutical composition. The isolated antibody may comprise sequence variants of SEQ ID NO: 25 and SEQ ID NO: 26, wherein such variants retain the ability to bind an epitope of IL-13 (SEQ ID NO:1) wherein said epitope comprises a position 10 arginine and a position 107 arginine of SEQ ID NO: 1, and the epitope may further comprise a residue selected from the group consisting of: a position 6 serine, a position 13 isoleucine, a position 14 glutamic acid, a position 100 leucine, a position 103 lysine, a position 106 phenylalanine, and a position 108 glutamic acid of SEQ ID NO:1;

An isolated humanized recombinant antibody comprising a humanized heavy chain variable region and humanized light chain variable region wherein the humanized heavy chain variable region comprises three complementarity determining regions (CDRS) from the heavy chain SEQ ID NO: 3 and a human framework region from a human acceptor antibody heavy chain, and the humanized light chain variable region comprises three complementarity determining regions from light chain SEQ ID NO: 2 and a human framework region from a human acceptor antibody light chain; wherein the humanized antibody reduces binding of IL-13 to an IL-13 receptor on THP-1 cells as measured by STATE signaling. The antibody substantially modulates an activity of IL-13 polypeptide selected from the group consisting of (a) inhibits human recombinant wild type human IL-13 binding to the human IL-13 receptor alpha 1 or a suitable animal IL-13 receptor as measured by wild type IL-13 induced Stat-6 phosphorylation, (b) inhibits human recombinant wild type human IL-13 binding to the human IL-13 receptor alpha 2 or a suitable animal IL-13 receptor, (c) decreases eosinophil, lymphocyte, macrophage and neutrophil cell numbers in the groups of rats treated with the antibody as compared to the saline-treated ova-sensitized animals, and (d) decreases airway resistance in chemically challenged animals as compared to a nonspecific control agent. The antibody may comprise CDRS from the heavy chain variable region selected from the group consisting of SEQ ID NO: 3, 20 and 26 and light chain variable region selected from the group consisting of SEQ ID NO: 2, 9, 14, and 26;

An antigen binding antibody fragment immunospecific for human IL-13 which binds to an the IL-13 variant R110Q with a $K_D$ as measured by plasmon surface resonance (Biacore) of less than 250 µM ($0.250 \times 10^{-9}$ M) and prevents binding of IL-13 to IL-13R2alpha1 on THP-1 cells as measured by STATE signaling and which antibody can be shown to contact human IL-13 at residues from helix A comprising Arg10, Ile13, Glu14 and residues from helix D comprising Lys103, Phe106, Arg107, Glu108, where the interatomic distances do not exceed 4.0 Å;

A method for diagnosing or treating an IL-13 related condition, including asthma, in a cell, tissue, organ or animal, comprising contacting or administering a composition comprising an effective amount (0.001-50 mg/kilogram) of an antibody described herein;

A method of immunizing a host using an IL-13 epitope comprising residues from helix A (Arg10, Ile13, Glu14) and residues from helix D (Lys103, Phe106, Arg107, Glu108) or a mimetic peptide thereof; and

BRIEF DESCRIPTION OF THE DRAWING

FIG. 1. Alignments of V-regions selected from the human framework libraries used for human adaptation of the murine C836 CDRs engrafted (within boxes) for light chain (upper alignment) and the heavy chain (lower alignment).

FIG. 2. Data obtained from an IL-13R-alpha2 competition binding assay for several high affinity mAbs generated using humanized variants of C863 where the L-CDR3 variant (specified) was paired with the heavy chain variant 2C02 and a biotinylated IL-13-WT was used at 500 pg/ml.

FIGS. 3A-3J. A table reflecting the different numbering schemes to define the structure of preferred antibodies.

BRIEF DESCRIPTION OF THE SEQUENCE LISTING

| SEQ ID NO: | Designation(s) | Description |
|---|---|---|
| 1 | IL-13, IL-13R130Q, IL-13R110Q | Human IL-13 mature chain (112 amino acids) and R110Q variant |
| 2 | C836 LCV, Lc16, 2A02 | Murine Mab C836 light chain variable region |
| 3 | C836 HCV, Hc7, 1A01 | Murine Mab C836 heavy chain variable region |
| 4 | Lc1, 1A02 | Human framework VB_A20 with C836 L-CDRs |
| 5 | Lc2, 1C03 | Human framework VB_O12 with C836 L-CDRs |
| 6 | Lc3, 1F03 | Human framework VB_L18 with C836 L-CDRs |

-continued

| SEQ ID NO: | Designation(s) | Description |
|---|---|---|
| 7 | Lc4, 1G02 | Human framework VB_A30 with C836 L-CDRs |
| 8 | Lc5, 3A01 | Human framework VB_L8 with C836 L-CDRs |
| 9 | Lc6, 3C09 | Human framework VB_L6 with C836 L-CDRs |
| 10 | Lc7, 3E02 | Human framework VB_O14 with C836 L-CDRs |
| 11 | Lc8, 4A01 | Human framework VB_L12 with C836 L-CDRs |
| 12 | Lc9, 4C07 | Human framework VB_L1-JK4 with C836 L-CDRs |
| 13 | Lc10, 4E01 | Human framework VB_L8-JK4 with C836 L-CDRs |
| 14 | Lc11, 4G04 | Human framework VB_L9-JK4 with C836 L-CDRs |
| 15 | Lc12, 5A09 | Human framework VB_L15-JK4 with C836 L-CDRs |
| 16 | Lc13, 5C03 | Human framework VB_L14-JK4 with C836 L-CDRs |
| 17 | Lc14, 7A01 | Human framework VB_L12-JK4 with C836 L-CDRs |
| 18 | Lc15, 6A06 | Human framework VB_L24-JK4 with C836 L-CDRs |
| 19 | Hc1, 2A01 | Human framework VB_2-70 with C836 H-CDRs |
| 20 | Hc2, 2C02 | Human framework VB_2-26 with C836 H-CDRs |
| 21 | Hc3, 2E01 | Human framework VB_2-05 with C836 H-CDRs |
| 22 | Hc4, 4E07 | Human framework VB_4-30 with C836 H-CDRs |
| 23 | Hc5, 3C04 | Human framework VB_4-28 with C836 H-CDRs |
| 24 | Hc6, 3E02 | Human framework VB_3-33 with C836 H-CDRs |
| 25 | M1295 | Engineered human framework light chain variable region |
| 26 | M1295 | Engineered human framework heavy chain variable region |
| 27 | Anti-IL-13 Lc | Variants of engineered human framework light chain variable region |
| 28 | Anti-IL-13 Hc | Variants of engineered human framework light chain variable region |
| 29 | LLc-CDR3 Variants | Active variants |

DETAILED DESCRIPTION

Abbreviations

CDR=Complementarity Determining Region; ELISA=Enzyme Linked Immunosorbent Assay; Fab=Antigen-Binding Fragment; He=Heavy chain of antibody; HFA=Human Framework Adapted; HV: hypervariable regions; IL-13 variant IL-13 R130Q (numbering from methionine #1 of the signal peptide) or IL-13 R110Q of the mature chain; Lc=Light chain of antibody; mAb=Monoclonal antibody; Ra1 or R alpha 1=human IL-13 receptor alpha 1; Ra2 or R alpha 2=human IL-13 receptor alpha 2; SDRU Specificity Determining Residue Usage; TBST Tris buffered saline with Tween.

Definitions

The terms "antigen binding domain," or "antigen-binding portion" of an antibody, as used herein, refer to one or more fragments of an antibody that retain the ability to specifically bind to an antigen (e.g., IL-13). It has been shown that the antigen-binding function of an antibody can be performed by fragments of a full-length antibody. Examples of binding fragments encompassed within the term "antigen-binding portion" of an antibody include a Fab fragment, a monovalent fragment having the VL, VH, CL and CH1 domains; a $F(ab)_2$ fragment, a bivalent fragment comprising two Fab fragments linked by a disulfide bridge(s) at a hinge region; a Fd fragment having the VH and CH1 domains; a Fv fragment having the VL and VH domains of a single arm of an antibody; a domain antibody or dAb fragment (Ward et al., 1989 Nature 341:544-546), which consists of a VH domain; and an isolated complementarity determining region (CDR), especially a CDR3 (See for example the WO03/025019, the contents of which are incorporated herein by reference).

The antigen-binding regions are defined using various terms. The term "Complementarity Determining Regions (CDRs)" is based on sequence variability (Wu and Kabat, J. Exp. Med. 132:211-250, 1970). There are six CDRs—three in the variable heavy chain, or VH, and are typically designated H-CDR1, H-CDR2, and H-CDR3, and three CDRs in the variable light chain, or VL, and are typically designated L-CDR1, L-CDR2, and L-CDR3 (Kabat et al., Sequences of Proteins of Immunological Interest, 5th Ed. Public Health Service, National Institutes of Health, Bethesda, Md., 1991). "Hypervariable region", "HVR", or "HV" refer to the regions of an antibody variable domain which are variable in structure as defined by Chothia and Lesk (Chothia and Lesk, Mol. Biol. 196:901-917, 1987). There are six HVRs, three in VH (H1, H2, H3) and three in VL (L1, L2, L3). Chothia and Lesk refer to structurally conserved HVs as "canonical structures." Another method of describing the regions that form the antigen-binding site has been proposed by Lefranc (Lefranc et al., Developmental & Comparative Immunology 27:55-77, 2003) based on the comparison of V domains from immunoglobulins and T-cell receptors (Lefranc et al., Developmental & Comparative Immunology 27:55-77, 2003). The antigen-binding site can also be delineated based on "Specificity Determining Residue Usage (SDRU)", according to Almagro (Almagro, Mol. Recognit. 17:132-43, 2004), where SDRU refers to amino acid residues of an immunoglobulin that are directly involved in antigen contact. A correspondence among different definitions of binding regions of exemplary antibodies described and claimed is presented in FIG. 3. We used herein Chothia's numbering and indel conventions (Al-lazikani et al., J. Mol. Biol. 1997) and CDRs as, CDR regions are defined as specific positions within the linear sequence of the VH or VL which takes into account the contributions or potential contributions of these residues to antigen binding.

Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv (scFv); see e.g., Bird et al., 1988 Science 242:423-426; and Huston et al., 1988 Proc. Nat. Acad. Sci. 85:5879-5883). Such single chain antibodies are encompassed by the term "antigen-binding portion" of an antibody. These antibody fragments are obtained using conventional techniques known to those of skill in the art, and the fragments are screened for utility in the same manner as intact antibodies.

An "isolated antibody," as used herein, refers to an antibody that is substantially free of other antibodies having different antigenic specificities (e.g., an isolated antibody that specifically binds IL-13 is substantially free of antibodies that specifically bind antigens other than IL-13). An isolated antibody that specifically binds IL-13 may, however, have cross-reactivity to other antigens, such as IL-13 molecules from other species. Moreover, an isolated antibody may be substantially free of other cellular material and/or chemicals.

The terms "monoclonal antibody," "Mab", or "monoclonal antibody composition" is generally understood to be an antibody, or composition of antibodies, such that an antibody is the product of a hybridoma capable of secreting only one type of antibody, or it is produced by a transfectoma, or it is an antibody made and isolated by recombinant methods from a hybridoma, a transfectoma, or a combinatorial human antibody library, or the antibody is prepared, expressed, created or isolated by any other means that involve splicing of all or a portion of a human immunoglobulin gene, sequences to other DNA sequences.

The term "humanized antibody", "engineered antibody", "human framework adapted", and "HFA" as used herein, is intended to include antibodies having variable region frameworks derived from sequences of human origin. Furthermore, if the antibody contains a constant region, the constant region is typically derived from such human sequences, e.g., human germline sequences, or naturally occurring (e.g., allotypes) or mutated versions of human germline sequences. The humanized antibodies of the invention may include amino acid residues not encoded by human sequences (e.g., mutations introduced by random or site-specific mutagenesis in vitro or by somatic mutation in vivo).

The term "interleukin-13" or "IL-13" is, except where context dictates otherwise, human IL-13 as represented by the mature chain shown in SEQ ID NO: 1. The present invention provides antibodies, particularly human or humanized antibodies, that bind to amino acid residues on human IL-13 and, insofar as these residues present a three-dimensional epitope within the IL-13 molecule, the monoclonal antibodies of the present invention may be expected to cross-react with non-human primate IL-13, including cynomolgus and rhesus monkey IL-13 or other IL-13 homologs from other species. Antibodies in accordance with the embodiments of the present invention bind a variant of IL-13 wherein an arginine residue at amino acid position 130 is replaced by glutamine.

As used herein, the term "high affinity" for an antibody refers to an antibody having a $K_D$ of $10^{-8}$ M or less, more preferably $10^{-9}$ M or less, and even more preferably $10^{-10}$ M or less. The term "$K_{dis}$" or "$K_D$" or "$K_d$" as used herein, is intended to refer to the dissociation rate of a particular antibody-antigen interaction. The "$K_D$", is the ratio of the rate of dissociation ($k_2$), also called the "off-rate ($k_{off}$)" or "$k_d$", to the rate of association rate ($k_1$) or "on-rate ($k_{on}$)" or "$k_a$". Thus, $K_D$ equals $k_2/k_1$ or $k_{off}/k_{on}$ or $k_d/k_a$ and is expressed as a molar concentration (M). It follows that the smaller $K_D$, the stronger the binding. Thus, a $K_D$ of $10^{-6}$M (or 1 μM) indicates weak binding compared to $10^{-9}$ M (or 1 nM).

As used herein, "specific binding" or "immunospecific binding" or "binds immunospecifically" refer to antibody binding to a predetermined antigen. Typically, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein, or another non-specific polypeptide) other than the predetermined antigen. The phrases "an antibody recognizing IL-13" and "an antibody specific for IL-13" are used interchangeably herein with the term "an antibody which binds immunospecifically to IL-13."

Antibodies—Characteristics

The subject matter disclosed and claimed herein relates to engineered anti-IL-13 antibodies that bind to IL-13 and preferably interfere with IL-13 activity or binding in vivo, in vitro, and/or in situ. A preferred anti-IL-13 antibody, specified portion thereof, or variant can also modulate IL-13 activity or function, such as, but not limited to, IL-13 receptor signaling, IL-13 receptor up- or down-regulation, IL-13 activity associated with receptor signaling, RNA, DNA or protein synthesis, protein release, including IgE and induction of major histocompatibility complex class II antigens and CD23.

The engineered antibodies may comprise any type of constant domains from any class of antibody, including IgM, IgG, IgD, IgA and IgE, and any subclass (isotype), including IgG1, IgG2, IgG3 and IgG4. When it is desired that the engineered antibody exhibit cytotoxic activity, the constant domain is usually a complement-fixing constant domain and the class is typically $IgG_1$. When such cytotoxic activity is not desirable, the constant domain may be of the IgG$_2$ class. The engineered antibody may comprise sequences from more than one class or isotype.

Nucleic acids encoding engineered light and heavy chain variable regions, optionally linked to constant regions, are inserted into expression vectors. The light and heavy chains can be cloned in the same or different expression vectors. The DNA segments encoding antibody amino acid sequences are operably linked to control sequences in the expression vector(s) that ensure the expression of immunoglobulin polypeptides. Such control sequences include a signal sequence, a promoter, an enhancer, and a transcription termination sequence (see Queen et al., Proc. Natl. Acad. Sci. USA 86, 10029 (1989); WO 90/07861; Co et al., J. Immunol. 148, 1149 (1992), which are incorporated herein by reference in their entirety for all purposes). Due to the redundancy in the genetic code, the DNA segments encoding immunoglobulin chains, subdomains or fragments thereof can be of varied composition selected from portions of naturally occurring human nucleic acid sequences, sequences hybridizable to such sequences, or totally artificial sequences encoding the amino acid sequences of the antibody.

Human monoclonal antibodies of the invention can be tested for binding to IL-13 by, for example, standard ELISA.

In one aspect, antibodies of the present invention comprise an IL-13-specific antibody, or IL-13 binding fragment thereof, specified portion thereof, or variant that modulates (preferably inhibits) an IL-13 mediated biological activity, in vitro, in vivo, or in situ, and exhibits one or more of the following criteria:
1. Binds human wild type recombinant or purified IL-13 (SEQ ID NO: 1), and the naturally occurring IL-13 variant Q110, or a fragment thereof, in a solid phase assay;
2. Has an apparent $K_d$ for human IL-13 wild type or specific mutant of less than 0.25 nM (as determined by surface plasmon resonance);
3. Inhibits human recombinant wild type human IL-13 binding to the human IL-13 receptor alpha 1, or to a non-human animal IL-13 receptor as measured by wild type IL-13 induced Stat-6 phosphorylation, which is an IL-13Rα1 specific signal transduction event;
4. Inhibits human recombinant wild type human IL-13 binding to the human IL-13 receptor alpha 2 or a suitable non-human animal IL-13 receptor;
5. Contacts IL-13 at residues on helix A (Arg10, Ile13, Glu14) and 5 residues from helix D (Leu100, Lys103, Phe106, Arg107, Glu108), where the interatomic distances do not exceed 4.0 Å.
6. Has a solubility of at least 10-100 mg/ml in PBS at pH 7.4, such as at least 10, 20, 30, 40, 50, 60, 70 or 80 mg/ml;
7. Prevents or suppresses proliferation of wild type human IL-13 dependent proliferation of human tumor THP-1 cells as compared to growth in the presence of a concentration of IL-13 without antibody present;
8. Inhibits human IL-13 wild type recombinant human IL-13 dependent in vitro IgE production in a fresh human B-cell preparation as compared to a fresh B-cell stimulated with the same concentration of IL-13 in the absence of antibody; and
9. Binds native wild type human IL-13 with potency similar to that for recombinant IL-13, as can be determined an IL-13 dependent bioassay or solid phase binding assay.

In another aspect of the invention, the structural features of the binding domains, are used to create structurally related human anti-IL-13 antibodies that retain a functional property of the antibodies of the invention, such as binding to IL-13. More specifically, one or more CDR regions of an antibody and variants as disclosed herein can be combined recombinantly with known human framework regions and CDRs to create additional, recombinantly-engineered, human anti-IL-13 antibodies of the invention.

For example, one approach taken to make IL-13 specific antibodies having one or more of the above described characteristics was to generate murine hybridomas from lymphoid tissue taken from mice immunized with the mature form of the human R130Q variant of IL-13 (SEQ ID NO: 1). Following immunization, a murine anti-human IL-13 R130Q monoclonal antibody was obtained and designated "C836." The C836 CDRs of the heavy and light chain variable regions (SEQ ID NO: 2 and 3, respectively) were grafted into selected human heavy chain and light chain frameworks and the binding affinity optimized. Specifically, the binding affinity of these Human Framework Adapted (HFA) antibodies for human IL-13 and variant IL-13 R130Q were enhanced by directed mutation either by randomization and selection from a phage-displayed Fab library, or by site directed mutagenesis, to develop a panel of heavy and light chains capable of high affinity binding to human IL-13 and the variant IL-13 R130Q (which also bears the designation "IL-13 R110Q"). Pairings of the affinity matured heavy and light chains described herein enables construction of complete antibodies having improved $K_D$ values which can be on the order of about 50 μM, and solubility greater than 100 mg/ml in phosphate buffered saline. The affinity-matured antibodies block binding of IL-13 to the IL-13 alpha 1 (Rα1) and alpha 2 (Rα2) receptors. The antibodies display these characteristics when expressed in mammalian expression systems such as human embryonic kidney 293 cells (HEK293) or Chinese hamster ovary (CHO) cells.

One mAb, in particular accepted for advanced characterization comprises a light chain from phage-mediated maturation of Lc6 (SEQ ID NO: 9) and a heavy chain from the site-directed mutagenesis of two methionines in the CDRs of Hc2 (SEQ ID NO: 20). This mAb was given the designation M1295 and comprises SEQ ID NOs: 25 and 26 as the Lc and Hc-variable regions, respectively, and may encoded by the corresponding nucleic acid sequences and expressed in a host cell or other system comprising components necessary for transcription and/or translation.

The invention further provides specified compositions and methods for preparation of the compositions comprising a variable domain selected from any one of SEQ ID NOs: 2 through 28 which have the desired characteristics and biological activity to treat an IL-13 mediated disorder. As stated above, in one embodiment the three heavy chain CDRs and the three light chain CDRs of the C836 antibody or antigen-binding fragment are used, as shown in Table 2. The recombinant antibodies preferably comprise the heavy and light chain CDR3 regions of C836, and variants thereof, as shown in Table 2 and those residues of the specified regions of SEQ ID NO: 27-29. The antibodies may further comprise the CDR2 domains of C836 and variants thereof. Still further, the antibodies of the invention may comprise the CDR1 domains of C836 and variants thereof. The invention may also provide anti-IL-13 antibodies comprising: (1) human heavy chain framework regions, and (2) human light chain framework regions along with preferred CDR domains. The human framework regions are substantially identical to the framework regions in SEQ ID NOs: 4 through 28. However, other framework regions combined with preferred CDR regions may be used to obtain antibodies having the desired properties for the target of interest (e.g., IL-13).

In addition, and as a non-limiting example, the antibody or antigen-binding portion or variant may comprise a heavy chain amino acid sequence of SEQ ID NOs: 19-24, and/or a light chain amino acid sequence of SEQ ID NO: 4-18. In a particular embodiment, the antibody or antigen-binding fragment can have an antigen-binding region that comprises a portion of a heavy chain comprising the amino acid sequence of SEQ ID NO: 28. In another particular embodiment, the antibody or antigen-binding portion or variant can have an antigen-binding region that comprises a portion of a light chain comprising the amino acid sequence of SEQ ID NO: 27. Such antibodies can be prepared by chemically joining together the various portions (e.g., CDRs, framework, etc.) of the antibody using conventional techniques, by preparing and expressing a nucleic acid molecule that encodes the heavy or light chain sequence(s) using conventional techniques of recombinant DNA technology or by using any other suitable method.

The CDR1, 2, and/or 3 domains of the engineered antibodies may consist of particular amino acid sequence(s) disclosed herein. Additionally, the CDR regions can tolerate sequence variability and retain their desired binding and biological characteristics. Accordingly, in another embodiment, the engineered antibody may comprise CDRs that are, for example, 90%, 95%, 98% or 99.5% identical to one or more CDRs of C836, as shown in Table 2 and variants as given in the specified positions of SEQ ID NO: 2-29. The framework regions of immunoglobulins are substantially identical or identical to the framework regions of the human germline variable regions from which they were derived. Many of the amino acids in the framework region make little or no direct contribution to the specificity or affinity of an antibody. Thus, many conservative substitutions of framework residues can be tolerated without appreciable change of the specificity or affinity of the resulting humanized immunoglobulin. The framework regions may be 90%, 95%, 98% or 99.5% identical to one or more of the frameworks described herein while allowing the variable regions of the immunoglobulin to retain the ability to contact residues of the target (e.g., IL-13). The variable segments of humanized antibodies produced as described supra are typically linked to at least a portion of a human immunoglobulin constant region. The antibody will contain both light chain and heavy chain constant regions. The heavy chain constant region usually includes CHL hinge, CH2, CH3, and, sometimes, CH4 domains.

The IL-13 antibody structure (or fragments thereof) may also be defined according to the three-dimensional crystal structure of the engineered IL-13 antibodies complexed with IL-13 or an IL-13 variant. The amino acid sequence of an IL-13 antibody may be altered, but nonetheless retain a three dimensional crystal structure which enables the engineered IL-13 antibodies to contact the IL-13 epitope and yield a neutralizing IL-13 specific antibody. Preferably, the antibody framework regions may be 90%, 95%, 98% or 99.5% identical to one or more of the frameworks described herein while allowing the variable regions of the immunoglobulin to retain the ability to contact specific residues of IL-13 from helix A (Arg10, Ile13, Glu14) and residues from helix D (Leu100, Lys103, Phe106, Arg107, Glu108), where the interatomic distances do not exceed 4.0 Å.

The IL-13 antibodies described herein may also be defined in terms of the paratope involved with binding IL-13. For example, antibodies having a paratope region which includes the residues of a light chain variable region numbered from the amino terminal residue as "1", given by L chain residues Tyr32, His91, Asn92 of SEQ ID NO: 2 and 9 residues from the H chain Tyr32, Trp54, Trp55, Asp56, Val58, Arg60, Asp103, Tyr104, Asp105 of SEQ ID NO: 3, numbered from the amino terminal residue as "1", are particular embodiments of such engineered antibodies. Another particular embodiment is an antibody that includes residues from the L chain Tyr32, His91, Asp92 (SEQ ID NO:25) and residues from the H chain Tyr32, Trp54, Trp55, Asp56, Val58, Arg60, Asp103, Tyr104, Asp105) of SEQ ID NO: 3.

In addition to binding IL-13, the engineered antibodies such as those described above may be selected for their retention of other functional properties of antibodies of the invention, such as the ability to inhibit the binding of Il-13 to IL-13R-alpha1 and preventing IL-13R-alpha1 signaling through STATE thereby blocking or reducing associated bioactivities in cells, tissues, and organs in vivo.

Method of Making and Testing the Anti-IL-13 Antibodies

An anti-IL-13 antibody of the present invention can be optionally generated by a variety of techniques, including the standard somatic cell hybridization technique (hybridoma method) of Kohler and Milstein (1975) Nature 256:495. In the hybridoma method, a mouse or other appropriate host animal, such as a hamster or macaque monkey, is immunized as described herein to elicit lymphocytes that produce or are capable of producing antibodies that will specifically bind to the protein used for immunization. Alternatively, lymphocytes may be immunized in vitro and fused with myeloma cells using a suitable fusing agent, such as polyethylene glycol, to form a hybridoma cell.

The anti-IL-13 antibody can also be generated by immunization of a transgenic animal (e.g., mouse, rat, hamster, non-human primate, and the like) capable of producing a repertoire of human antibodies, as described herein and/or as known in the art. Cells that produce a human anti-IL-13 antibody can be isolated from such animals and immortalized using suitable methods, such as the methods described as hybridomas or other methods know in the art. Alternatively, the antibody coding sequences may be cloned, introduced into a suitable vector, and used to transfect a host cell for expression and isolation of the antibody by methods taught herein and those known in the art.

The use of transgenic mice carrying human immunoglobulin (Ig) loci in their germline configuration provide for the isolation of high affinity fully human monoclonal antibodies directed against a variety of targets including human self antigens for which the normal human immune system is tolerant (see for example Lonberg, N. et al., U.S. Pat. No. 5,569,825, U.S. Pat. No. 6,300,129; Kucherlapati, et al., U.S. Pat. No. 6,713,610). The endogenous immunoglobulin loci in such mice can be disrupted or deleted to eliminate the capacity of the animal to produce antibodies encoded by endogenous genes. In addition, companies such as Abgenix, Inc. (Fremont, Calif.) and Medarex (San Jose, Calif.) can be engaged to provide human antibodies directed against a selected antigen using technology as described above.

Antibodies obtained from non-human sources can be humanized. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is one containing one or more immunoglobulin chains comprising a CDR derived from an antibody of nonhuman origin and a framework region derived from a light and/or heavy chain of human origin (e.g., CDR-grafted antibodies with or without framework changes). The framework adaptation process was based upon the similarity of framework regions between mouse mAb C836 and sequences in the human germline databases as essentially described in WO/08052108A2 "Methods For Use In Human-Adapting Monoclonal Antibodies" where framework length is matched residue for residue to the parental variable or V-regions. In total, sixteen light chain (LC) and six heavy chain (HC) frameworks were human framework adapted by combing the C836 CDRs with selected human frameworks.

In one embodiment, the human antibody is selected from a phage library, where that phage comprises human immunoglobulin genes and the library expresses human antibody binding domains as, for example, single chain antibodies (scFv), as Fab, or some other construct exhibiting paired or unpaired antibody variable regions fused to one or more of the phage coat proteins. Such phage display methods for isolating human antibodies are established in the art, see for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

The isolated nucleic acids of the present invention can be made using (a) recombinant methods; (b) synthetic techniques; (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of murine antibodies). Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For commercial manufacture, the antibody encoding DNA will be transfected into a suitable host cell, stable clones isolated, and the cell line expanded into a master cell bank.

Method of Using the Anti-IL-13 Antibodies

The present invention also provides a method for modulating or treating an IL-13 related disease, in a cell, tissue, organ, animal, or patient, as known in the art or as described herein, using an anti-IL-13 antibody of the present invention. The present invention provides a method for modulating or treating an IL-13 related disease, in a cell, tissue, organ, animal, or patient including, but not limited to, a fibrotic disease, neoplastic, metabolic, an immune or inflammatory related disease, a cardiovascular, an infectious, a dermatologic, or a neurologic disease. The subject matter disclosed herein also includes the use of an anti-IL-13 antibody described herein in the manufacture of a medicament for the treatment of an IL-13 mediated disorder, including, but not limited to asthma, atopic dermatitis, allergic rhinitis, and related respiratory disorders, and other IL-13 mediated disorders described herein.

Interleukin 13 (IL-13) is associated with type II inflammatory responses illustrated with the atopic triad of asthma, atopic dermatitis and allergic rhinitis. Emerging evidence links the IL-13 pathway in the pathogenesis of eosinophilic esophagitis (EE), an eosinophilic-mediated gastrointestinal disease. Additionally, IL-13 is associated with non-atopic disease pathology related to both inflammation and tissue remodeling observed in non-atopic subjects with asthma and chronic obstructive pulmonary disease (COPD), and in patients with fibrotic diseases including systemic sclerosis (SSc), and idiopathic pulmonary fibrosis (IPF). The rationale for targeting IL-13 is that both atopic and non-atopic responses in specific disease subsets is driven by IL-13, and that antagonism of the IL-13 protein will abrogate such responses.

Respiratory Disease

The present invention also provides a method for modulating or treating a bronchial, pulmonary or pleural disease in a cell, tissue, organ, animal or patient, including, but not limited to: asthma; pneumonia; lung abscess; occupational lung diseases caused by inspired or inhaled agents; and respiratory failure and conditions or causes leading to respiratory failure. The present invention also provides a method for modulating or treating hyperactive airway disease; bronchiolitis fibrosa obliterans; hypersensitivity diseases of the lungs including hypersensitivity pneumonitis (extrinsic allergic alveolitis), allergic bronchopulmonary aspergillosis, and drug reactions; adult respiratory distress syndrome (ARDS), Goodpasture's Syndrome, chronic obstructive airway disorders (COPD), idiopathic interstitial lung diseases such as idiopathic pulmonary fibrosis and sarcoidosis; desquamative interstitial pneumonia; acute interstitial pneumonia; respiratory bronchiolitis-associated interstitial lung disease; idiopathic bronchiolitis obliterans with organizing pneumonia; lymphocytic interstitial pneumonitis; Langerhans' cell granulomatosis; idiopathic pulmonary hemosiderosis; acute bronchitis; pulmonary alveolar proteinosis; bronchiectasis; atelectasis; cystic fibrosis; tumors of the lung; and pulmonary embolism.

Neoplastic Disease

The present invention also provides a method for modulating or treating a malignant and neoplastic disease in a cell, tissue, organ, animal or patient, including, but not limited to: leukemia; acute leukemia; acute lymphoblastic leukemia (ALL); B-cell, T-cell or FAB ALL; acute myeloid leukemia (AML); chronic myelocytic leukemia (CML); chronic lymphocytic leukemia (CLL); hairy cell leukemia; myelodysplastic syndrome (MDS); a lymphoma, especially non-Hodgkin's lymphoma, Hodgkin's disease, a non-malignant lymphoma, Burkitt's lymphoma; multiple myeloma; solid tumors as primary disease or as metastatic disease; Kaposi's sarcoma; colorectal carcinoma; prostate cancer; testicular cancer; renal cell carcinoma; lung cancer including mesothelioma; breast cancer including inflammatory breast cancer; nasopharyngeal carcinoma; malignant histiocytosis, paraneoplastic syndrome/hypercalcemia of malignancy; adenocarcinomas; squamous cell carcinomas, particularly of the head and neck; sarcomas; malignant melanoma, particularly metastatic melanoma; hemangioma; metastatic disease; cancer related bone resorption; cancer related bone pain; and the like. In addition, the antibody of the present invention may be used to treat primary or secondary tumors of the endocrine organs such as the pituitary, thyroid, adrenals, pancreas, thereby also improving, preventing or ameliorating such related disorders as galactorrhea, short stature, gigantism and acromegaly, diabetes insipidus, diabetes, Addison's disease, Cushing's syndrome, aldosteronism, adrenal insufficiency, pheochromocytoma, acid-base disorders, and porphyrias.

Immune Related and Inflammatory Diseases

The present invention also provides a method for modulating or treating an immune related disease, in a cell, tissue, organ, animal, or patient including, but not limited to rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/Wegener's granulomatosis, sarcoidosis, orchitis/vasectomy reversal procedures, allergic/atopic diseases, asthma, allergic rhinitis, atopic dermatitis (eczema), esophagitis, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol induced hepatitis, chronic inflammatory pathologies, Crohn's pathology, sickle cell anemia, diabetes, nephrosis, other atopic diseases, hypersensitivity reactions, allergic rhinitis, hay fever, perennial rhinitis, conjunctivitis, endometriosis, asthma, urticaria, systemic anaphylaxis, dermatitis, pernicious anemia, hemolytic diseases, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, metabolic or idiopathic drug sensitivity, Wilson's disease, hemachromatosis, alpha-1-antitrypsin deficiency, diabetic retinopathy, Hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, and inflammation due to anti-CD3 therapy, cytokine therapy, chemotherapy, radiation therapy (e.g., including but not limited to asthenia, anemia, cachexia, and the like), chronic salicylate intoxication, and the like.

In addition, the anti-IL-13 antibody, fragment, or variant thereof may be used to treat diseases eosinophile-mediated inflammation; eosinophile-mediated esophagitis, lung, tracheal, alveolar or asthma related inflammation; such as eosinphilic gastrointestinitis, gastric or intestinal inflammation; and, in particular, where STAT6-mediated signaling causes such eosinophilic inflammation, such as in STAT6-mediated gastrointestinal inflammation and eosinophilic esophagitis.

Cardiovascular Disease

The present invention also provides a method for modulating or treating a cardiovascular disease in a cell, tissue, organ, animal, or patient, related to or stemming from: arrhythmias and conduction disorders; arterial hypertension; arteriosclerosis; cardiac tumors; cardiomyopathies; coronary artery disease; aortitis and aortic branch occlusion; endocarditis; pulmonary edema; pericarditis; and peripheral, arterial, venous and lymphatic disorders; and valvular disorders. The present invention also provides a method for modulating or treating a cardiovascular disease in a cell, tissue, organ, animal, or patient, including, but not limited to, cardiac stun syndrome, myocardial infarction, congestive heart failure, stroke, ischemic stroke, hemorrhage, restenosis, diabetic ateriosclerotic disease, hypertension, arterial hypertension, renovascular hypertension, syncope, shock, heart failure, cor pulmonale, primary pulmonary hypertension, cardiac arrhythmias, post perfusion syndrome, cardiopulmonary bypass inflammation response, chaotic or multifocal atrial tachycardia, regular narrow QRS tachycardia, specific arrhythmias, ventricular fibrillation, His bundle arrhythmias, atrioventricular block, bundle branch block, myocardial ischemic disorders, angina pectoris, myocardial infarction, cardiomyopathy, dilated congestive cardiomyopathy, restrictive cardiomyopathy, aortic and peripheral aneuryisms, aortic dissection, inflammation of the aorta, thromboangitis obliterans, functional peripheral arterial disorders, Raynaud's phenomenon and disease, acrocyanosis, erythromelalgia, venous thrombosis, varicose veins, arteriovenous fistula, lymphederma, edema, unstable angina, reperfusion injury, post pump syndrome, ischemia-reperfusion injury, and the like.

Neurologic Disease

The present invention also provides a method for modulating or treating a neurologic disease including causes or sequelae of disturbances of one or more of: cerebrospinal fluid and its circulation; intracranial neoplasms and paraneoplastic disorders; infections of the nervous system (bacterial, fungal, spirochetal, parasitic, viral or prions); sarcoidosis; cerebrovascular diseases; craniocerebral trauma; multiple sclerosis and allied demyelinative diseases; inherited and developmental diseases of the nervous system; metabolic disorders of the nervous system; disorders of the nervous system due to alcohol, drugs, toxins, and other chemical agents; diseases of the spinal cord; and diseases of the peripheral nerve and muscle. The present invention also provides a method for modulating or treating at neurologic disease in a cell, tissue, organ, animal or patient, including, but not limited to: neurodegenerative diseases; multiple sclerosis; migraine headache; AIDS dementia complex; acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supra-nucleo Palsy; structural lesions of the cerebellum; spinocerebellar degenerations, such as spinal ataxia; Friedreich's ataxia; cerebellar cortical degenerations; multiple systems degenerations (Mencel, Dejerine-Thomas, Shi-Drager, and Machado-Joseph); systemic disorders (Refsum's disease, abetalipoprotemia, ataxia telangiectasia, and mitochondrial multi-system disorder); demyelinating core disorders, such as multiple sclerosis; acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome related mental disorders; diffuse Lewy body disease; Senile dementia of Lewy body type; Wernicke-Korsakoff syndrome; mental disorders associated with chronic alcoholism; prion diseases such as Creutzfeldt-Jakob disease; subacute sclerosing panencephalitis; Hallerrorden-Spatz disease; dementia pugilistica, and the like. Such a method can optionally comprise administering an effective amount of a composition or pharmaceutical composition comprising an anti-IL-13 antibody or specified portion or variant to a cell, tissue, organ, animal or patient in need of such modulation, treatment or therapy.

Other Therapeutic Uses of Anti-IL-13 Antibodies

In addition to the above described conditions and diseases, the present invention also provides a method for modulating or treating fibrotic conditions of various etiologies such as liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular nephritis, lupus nephritis); dermal fibrosis (including but not limited to scleroderma, hypertrophic and keloid scarring, burns); myelofibrosis; neurofibromatosis; fibroma; intestinal fibrosis; and fibrotic adhesions resulting from surgical procedures including organ or transplantation.

The present invention also provides a method for modulating or treating an infectious disease in a cell, tissue, organ, animal or patient, including, but not limited to: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, E. coli, hemolytic uremic syndrome, malaria, dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis/epidymitis, legionella, lyme disease, influenza a, Epstein-Barr virus, vital-associated hemaphagocytic syndrome, vital encephalitis/aseptic meningitis, and the like.

The present invention also provides a method for modulating or treating disease of the eye due to inflammation, infection, or fibrotic or stenotic conditions such as but not limited to: conjunctivitis, corneal ulcer, keratoconus, interstitial keratitis, peripheral ulcerative keratitis, phlyctenular conjunctivitis, superficial punctate keratitis, blepharitis, uveitis, and age-related macular degeneration.

Administration, Compositions, and Kits Comprising the Anti-IL-13 Antibodies

Whereas, an isolated monoclonal antibody of the present invention binds an epitope on IL-13 and displays in vitro and/or in vivo IL-13 inhibiting activities, the antibodies or antigen binding fragments thereof, capable of inhibiting IL-13 binding to receptors IL-13R1alpha and IL-13R2alpha, are suitable both as therapeutic and prophylactic agents for treating or preventing IL-13-associated conditions in humans and animals.

In general, use will comprise administering a therapeutically or prophylactically effective amount of one or more monoclonal antibodies or antigen binding fragments of the present invention to a susceptible subject or one exhibiting a condition in which IL-13 activity is known to have pathological sequelae such as tumor growth and metastasis or asthmatic symptoms such as reduction in forced expiration volume (FEV). Any active form of the antibody can be administered, including Fab and F(ab')2 fragments.

Preferably, the antibodies used are compatible with the recipient species such that the immune response to the MAbs does not result in an unacceptably short circulating half-life or induce an immune response to the MAbs in the subject. Preferably, the MAbs administered exhibit some secondary functions such as binding to Fc receptors of the subject and activation of antibody dependent cell mediated cytotoxicity (ADCC) mechanisms.

Treatment of individuals may comprise the administration of a therapeutically effective amount of the antibodies of the present invention. The antibodies can be provided in a kit as described below. The antibodies can be used or administered alone or in admixture with another therapeutic, analgesic, or diagnostic agent. In providing a patient with an antibody, or fragment thereof, capable of binding to IL-13, or an antibody capable of protecting against IL-13 in a recipient patient, the dosage of administered agent will vary depending upon such factors as the patient's age, weight, height, sex, general medical condition, previous medical history, etc.

Suitable vehicles and their formulation and packaging are described, for example, in Remington: The Science and Practice of Pharmacy (21st ed., Troy, D. ed., Lippincott Williams & Wilkins, Baltimore, Md. (2005) Chapters 40 and 41). Additional pharmaceutical methods may be employed to control the duration of action. Controlled release preparations may be achieved through the use of polymers to complex or absorb the compounds. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions.

In general, if administering a systemic dose of the antibody, it is desirable to provide the recipient with a dosage of antibody which is in the range of from about 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg (body weight of recipient), although a lower or higher dosage may be administered. Dosages as low as about 1.0 mg/kg may be expected to show some efficacy. Preferably, about 5 mg/kg is an acceptable dosage, although dosage levels up to about 50 mg/kg are also preferred especially for therapeutic use. Alternatively, administration of a specific amount of the antibody may be given which is not based upon the weight of the patient such as an amount in the range of 1 ug-100 ug, 1 mg-100 mg, or 1 gm-100 gm. For example, site specific administration may be to body compartment or cavity such as intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, or transdermal means.

The IL-13 antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents;

or transdermally such as not limited to a gel, ointment, lotion, suspension or patch delivery system with chemical enhancers to either modify the skin structure or to increase the drug concentration in the transdermal patch, or with agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

In a similar approach, another therapeutic use of the monoclonal antibody of the present invention is the active immunization of a patient using an anti-idiotypic antibody raised against one of the present monoclonal antibodies. Immunization with an anti-idiotype which mimics the structure of the epitope could elicit an active anti-IL-13 response.

Likewise, active immunization can be induced by administering one or more antigenic and/or immunogenic epitopes as a component of a vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used e.g., NH2-acetylation or COOH-terminal amidation, to provide additional means for coupling or fusing the peptide to another protein or peptide molecule or to a support. An embodiment of an immunogenic epitope is one that encompasses residues of IL-13 from helix A (Arg10, Ile13, Glu14) and residues from helix D (Leu100, Lys103, Phe106, Arg107, Glu108). In a particular embodiment of a peptide or protein comprising antigen epitope, the peptide displays a mimitope which mimics the spatial association of Arg10 and Arg107 of IL-13 or variants as shown by X-ray crystallography.

An antibody of the invention, capable of protecting against IL-13 bioactivity, is intended to be provided to subjects in an amount sufficient to affect a reduction, resolution, or amelioration in the IL-13-related symptom or pathology. An amount is said to be sufficient or a "therapeutically effective amount" to "affect" the reduction of symptoms if the dosage, route of administration, and dosing schedule of the agent are sufficient to influence such a response. Responses to antibody administration can be measured by analysis of subject's affected tissues, organs, or cells as by imaging techniques or by ex vivo analysis of tissue samples. An agent is physiologically significant if its presence results in a detectable change in the physiology of a recipient patient.

The antibodies of the present invention can be formulated according to known methods to prepare pharmaceutically useful compositions, whereby these materials, or their functional derivatives, are combined in admixture with a pharmaceutically acceptable carrier vehicle. The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container containing or packaged in association with the above-described antibodies. The kit may also comprise another container containing or packaged in association solutions necessary or convenient for carrying out the invention. The containers can be made of glass, plastic or foil and can be a vial, bottle, pouch, tube, bag, etc. The kit may also contain written information, such as procedures for carrying out the present invention or analytical information, such as the amount of reagent contained in the first container means. The container may be in another container apparatus, e.g. a box or a bag, along with the written information.

Yet another aspect of the present invention is a kit for detecting IL-13 in a biological sample. The kit includes a container holding one or more antibodies which binds an epitope of IL-13 and instructions for using the antibody for the purpose of binding to IL-13 to form an immunological complex and detecting the formation of the immunological complex such that the presence or absence of the immunological complex correlates with presence or absence of IL-13 in the sample. Examples of containers include multiwell plates which allow simultaneous detection of IL-13 in multiple samples.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

EXAMPLE 1

Anti-IL-13 Antibody Production

The murine hybridoma, C836, was made against a natural variant of human IL-13, R130Q, which is the R110Q variant of SEQ ID NO: 1. Two 12-14 week old Balb/c mice (Charles River Laboratories) designated numbers 72 and 75 were used. Mouse #72 received a total of three biweekly 50 mg injections of human IL-13 R130Q given intraperitoneally (IP) and intradermally (ID) in Gerbu adjuvant (Accurate). Mouse #75 was immunized subcutaneously (SQ) at the base of tail (BOT) with 50 mg R130Q in combination with $0.33 \times 10^5$ units each of murine interferon-a and b (Biosource). On days 2 and 3, the mice were injected SQ BOT with the interferon-a and b (same doses as on day 1). Two booster injections of 50 mg R130Q in combination with 100 mg anti-murine CD40 agonist Mab (R&D) given SQ BOT were performed on days 58 and 85. Antibody titers were screened from blood collected by retro-orbital puncture. A R130Q solid phase EIA assay was performed to assess serum titers for anti-R130Q IgG.

For the fusion designated MattA, mouse #72 was IV boosted with 50 mg of R130Q diluted to 100 mL in phosphate buffered saline (PBS). For the fusion named MattB, mouse #75 received a final booster of 15 mg R130Q in combination with 50 mg anti-murine CD40 agonist SQ BOT. Three days after the final booster injections, the mice were sacrificed, the lymphoid organs removed aseptically, and the immune lymphocytes harvested by grinding the spleen and/or lymph nodes through a fine mesh screen with a small pestle and rinsing with warm DMEM.

A solid phase EIA was used to screen murine sera for antibodies specific for the naturally occurring variant of human IL-13 (R130Q) using 96-well plates (Costar, 9018) coated with goat anti-murine IgG-Fc. Mouse serum was serially diluted two-fold in PBS starting from a 1:50 dilution and incubated at 50 ul/well for 1 hour at 37° C. The plates were washed and then incubated with 300 ng/ml, 50 ml/well biotinylated R130Q for one hour at 37° C. The plates were washed, probed with peroxidase-conjugated streptavidin, and developed with $H_2O_2$ and OPD. The absorbance was measured at 490 nm via an automated plate spectrophotometer.

The non-secreting Balb/c mouse myeloma fusion partner, FO was purchased from ATCC(CRL-1646). The MattA fusion was carried out at a 1:2 ratio of FO murine myeloma cells to viable spleen cells. For the MattB fusion, lymphocytes from the spleen and popliteal/inguinal lymph nodes (LN) were pooled to perform the fusion. The fusion was carried at a 1:1 ratio of murine myeloma cells (FO) to viable lymphocytes. The fused cells were resuspended in HAT medium (100 µM hypoxanthine, 0.4 µM aminopterin, and 16 µM thymidine), plated at 200 µL/well in 25×96-well plates, and incubated for 7-10 days.

Hybridomas arising from the fusion of murine lymphocytes with murine myeloma cells were evaluated by EIA for their ability to bind mature R130Q (IL-13 R110Q variant of SEQ ID NO: 1). Cells in positive wells were transferred to 24-well plates to increase cell numbers and later subcloned by limiting dilution to ensure homogeneity of the cell lines. The Mouse Monoclonal Antibody Isotyping Kit-IsoStrip, Dipstick Format (Roche) was used as per the manufacturer instructions to determine isotype.

Twelve R130Q reactive MAbs were determined from MattA fusion and three from MattB fusion via EIA. Thirteen antibodies were identified as murine IgG1/κ, one as IgG2aκ and one as IgG1/λ isotype. Homogeneous hybridoma cell lines were assigned C code designations and respective MAbs assigned CNTO numbers (Table 1).

TABLE 1

Murine anti-Human IL-13 (R130Q) MAbs

| Hybridoma Name | Cell-code # | CNTO # | Murine Isotype |
| --- | --- | --- | --- |
| MattA-103.10.1 | 850 | 1103 | IgG1/κ |
| MattA-122.23.3 | 830 | 2223 | IgG1/κ |
| MattA-129.10.2 | 831 | 2910 | IgG1/κ |
| MattA-132.6.2 | 870 | 62 | IgG2a/κ |
| MattA-137.4.2 | 832 | 3742 | IgG1/κ |
| MattA-141.40.3 | 833 | 403 | IgG1/κ |
| MattA-145.1.2 | 834 | 1451 | IgG1/κ |
| MattA-16.1.2 | 827 | 1612 | IgG1/κ |
| MattA-167.6.2 | 835 | 1676 | IgG1/κ |
| MattA-173.3.3 | 836 | 1733 | IgG1/κ |
| MattA-29.12.3 | 828 | 2912 | IgG1/κ |
| MattA-60.42.2 | 829 | 6042 | IgG1/λ |
| MattB-1.2.2 | 915 | 2122 | IgG1/κ |
| MattB-3.4.2 | 916 | 2342 | IgG1/κ |
| MattB-2.2.1 | 919 | 2221 | IgG1/κ |

The cDNA of the light and heavy chains for the murine hybridoma were cloned by room temperature-PCR and sequenced. The cDNAs were inserted into Lonza eukaryotic expression vectors pEE12.4 and pEE6.4 for the light chain and heavy chain, respectively, under control of the CMV promoter and containing the GS selectable gene marker. C836 mAb from the cloned sequences were transiently transfected into HEK293 cells and assayed against the antibody secreted from the hybridoma. The CDRs from the V-regions are shown below (Table 2) and in the sequence listing for the light and heavy chain V-regions (SEQ ID NO: 2 and 3, respectively).

TABLE 2

CDRs From Mouse Hybridoma C836 Targeting Human IL-13

| CDR | Amino Acid Sequence | Residues and Corresponding SEQ ID NO: |
| --- | --- | --- |
| L CDR1 | RASKSISKYLA | 24-34 of SEQ ID NO: 2 |
| L CDR2 | SGSTLQS | 50-56 of SEQ ID NO: 2 |
| L CDR3 | QQHNEYPYT | 89-97 of SEQ ID NO: 2 |
| H CDR1 | GFSLSTYGMGVG | 26-37 of SEQ ID NO: 3 |
| H CDR2 | HIWWDDVKRYNPALKS | 52-67 of SEQ ID NO: 3 |
| H CDR3 | MGSDYDVWFDY | 100-110 of SEQ ID NO: 3 |

The activity of the purified mAb expressed from the cloned sequences was verified to be the same as the activity observed in conditioned media from hybridoma C836. The activity was measured using an assay to evaluate the inhibition of binding of 150 ng/ml biotinylated IL-13 to IL-13R-alpha2.

EXAMPLE 2

Creation of Human Framework Adapted (HFA) Library

The process of humanization of mAb C836 involved two general processes: 1) framework adaptation; and 2) affinity maturation largely from within selected frameworks. In addition, certain residues were modified to promote protein stability.

The framework adaptation process was based upon the similarity of framework regions between mouse mAb C836 and sequences in the human germline databases as essentially described in WO/08052108A2 "Methods For Use In Human-Adapting Monoclonal Antibodies" where framework length is matched residue for residue to the parental variable or V-regions. In total, sixteen light chain (LC) and six heavy chain (HC) frameworks were human framework adapted by combing the C836 CDRs with selected human frameworks as shown in Table 3 (LC) and 4 (HC). CDRs are highlighted by underlining in both tables.

The light chain frameworks O12 (SEQ ID NO: 5), L6 (SEQ ID NO: 9), L12 (SEQ ID NO: 11), and L18 (SEQ ID NO: 6), have the highest similarity to the murine V-region (SEQ ID NO: 2) (FIG. 1 upper alignment). For the heavy chain CDRs, human frameworks 2-26 (SEQ ID NO: 20), and 2-05 (SEQ ID NO: 21), have the highest similarity to the murine V-region (SEQ ID NO: 3) (FIG. 1 lower alignment).

TABLE 3

Light Chain Framework & CDR Sequences

| No. | Framework | F1<br>CDR1<br>F2<br>CDR2<br>F3<br>CDR3<br>F4 | SEQ ID NO: |
|---|---|---|---|
| L1 | VB_A20 | DIQMTQSPSSLSASVGDRVTITC<br>RASKSISKYLA<br>WYQQKPGKVPKLLIY<br>SGSTLQS<br>GVPSRFSGSGSGTDFTLTISSLQPEDVATYYC<br>QQHNEYPYT<br>FGGGTKVEIK | 4 |
| L2 | VB_O12 | DIQMTQSPSSLSASVGDRVTITC<br>RASKSISKYLA<br>WYQQKPGKAPKLLIY<br>SGSTLQS<br>GVPSRFSGSGSGTDFTLTISSLQPEDFATYYC<br>QQHNEYPYT<br>FGQGTKLEIK | 5 |
| L3 | VB_L18 | AIQLTQSPSSLSASVGDRVTITC<br>RASKSISKYLA<br>WYQQKPGKAPKLLIY<br>SGSTLQS<br>GVPSRFSGSGSGTDFTLTISSLQPEDFATYYC<br>QQHNEYPYT<br>FGGGTKVEIK | 6 |
| L4 | VB_A30 | DIQMTQSPSSLSASVGDRVTITC<br>RASKSISKYLA<br>WYQQKPGKAPKRLIY<br>SGSTLQS<br>GVPSRFSGSGSGTEFTLTISSLQPEDFATYYC<br>QQHNEYPYT<br>FGGGTKVEIK | 7 |
| L5 | VB_L8 | DIQLTQSPSFLSASVGDRVTITC<br>RASKSISKYLA<br>WYQQKPGKAPKLLIY<br>SGSTLQS<br>GVPSRFSGSGSGTEFTLTISSLQPEDFATYYC<br>QQHNEYPYT<br>FGGGTKVEIK | 8 |
| L6 | VB_L6 | EIVLTQSPATLSLSPGERATLSC<br>RASKSISKYLA<br>WYQQKPGQAPRLLIY<br>SGSTLQS<br>GIPARFSGSGSGTDFTLTISSLEPEDFAVYYC<br>QQHNEYPYT<br>FGQGTKLEIK | 9 |
| L7 | VB_O14 | DIQLTQSPSSLSASVGDRVTITC<br>RASKSISKYLA<br>WYRQKPGKVPKLLIY<br>SGSTLQS<br>GVPSRFSGSGSGTDFTLTISSLQPEDVATYYG<br>QQHNEYPYT<br>FGQGTKLEIK | 10 |
| L8 | VB_L12 | DIQMTQSPSTLSASVGDRVTITC<br>RASKSISKYLA<br>WYQQKPGKAPKLLIY<br>SGSTLQS<br>GVPSRFSGSGSGTEFTLTISSLQPDDFATYYC<br>QQHNEYPYT<br>FGQGTRLEIK | 11 |
| L9 | VB_L1-JK4 | DIQMTQSPSSLSASVGDRVTITC<br>RASKSISKYLA<br>WFQQKPGKAPKSLIY<br>SGSTLQS<br>GVPSRFSGSGSGTDFTLTISSLQPEDFATYYC<br>QQHNEYPYT<br>FGGGTKVEIK | 12 |
| L10 | VB_L8-JK4 | DIQLTQSPSFLSASVGDRVTITC<br>RASKSISKYLA<br>WYQQKPGKAPKLLIY<br>SGSTLQS<br>GVPSRFSGSGSGTEFTLTISSLQPEDFATYYC<br>QQHNEYPYT<br>FGGGTKVEIK | 13 |
| L11 | VB_L9-JK4 | AIRMTQSPSSFSASTGDRVTITC<br>RASKSISKYLA<br>WYQQKPGKAPKLLIY<br>SGSTLQS<br>GVPSRFSGSGSGTDFTLTISCLQSEDFATYYC<br>QQHNEYPYT<br>FGGGTKVEIK | 14 |
| L12 | VB_L15-JK4 | DIQMTQSPSSLSASVGDRVTITC<br>RASKSISKYLA<br>WYQQKPEKAPKSLIY<br>SGSTLQS<br>GVPSRFSGSGSGTDFTLTISSLQPEDFATYYC<br>QQHNEYPYT<br>FGGGTKVEIK | 15 |
| L13 | VB_L14-JK4 | NIQMTQSPSAMSASVGDRVTITC<br>RASKSISKYLA<br>WFQQKPGKVPKHLIY<br>SGSTLQS<br>GVPSRFSGSGSGTEFTLTISSLQPEDFATYYC<br>QQHNEYPYT<br>FGGGTKVEIK | 16 |
| L14 | VB_L12-JK4 | DIQMTQSPSTLSASVGDRVTITC<br>RASKSISKYLA<br>WYQQKPGKAPKLLIY<br>SGSTLQS<br>GVPSRFSGSGSGTEFTLTISSLQPDDFATYYC<br>QQHNEYPYT<br>FGGGTKVEIK | 17 |
| L15 | VB_L24-JK4 | VIWMTQSPSLLSASTGDRVTISC<br>RASKSISKYLA<br>WYQQKPGKAPELLIY<br>SGSTLQS<br>GVPSRFSGSGSGTDFTLTISCLQSEDFATYYC<br>QQHNEYPYT<br>FGGGTKVEIK | 18 |
| L16 | C836 LCV-region, Murine Parent | DVQITQSPSYLAASPGETITLNC<br>RASKSISKYLA<br>WYQEKPGKTNKLLIY<br>SGSTLQS<br>GIPSRFSGSGSGTDFTLTISSLEPEDFAMYFC<br>QQHNEYPYT<br>FGGGTKLEIK | 2 |

TABLE 4

Heavy Chain Framework & CDR Sequences

| No. | Framework | F1<br>CDR1<br>F2<br>CDR2<br>F3<br>CDR3<br>F4 | SEQ ID NO: |
|---|---|---|---|
| H1 | VB_2-70 | QVTLKESGPALVKPTQTLTLTCTFS<br>GFSLSTYGMGVG<br>WIRQPPGKALEWLA<br>HIWWDDVKRYNPALKS<br>RLTISKDTSKNQVVLTMTNMDPVDTATYY<br>CAR<br>MGSDYDVWFDY<br>WGQGTLVTVSS | 19 |
| H2 | VB_2-26 | QVTLKESGPVLVKPTETLTLTCTVS<br>GFSLSTYGMGVG<br>WIRQPPGKALEWLA<br>HIWWDDVKRYNPALKS<br>RLTISKDTSKSQVVLTMTNMDPVDTATYY<br>CAR<br>MGSDYDVWFDY<br>WGQGTLVTVSS | 20 |
| H3 | VB_2-05 | QITLKESGPTLVKPTQTLTLTCTFS<br>GFSLSTYGMGVG<br>WIRQPPGKALEWLA<br>HIWWDDVKRYNPALKS<br>RLTITKDTSKNQVVLTMTNMDPVDTATYY<br>CA<br>MGSDYDVWFDY<br>WGQGTLVTVSS | 21 |
| H4 | VB_4-30. | QVQLQESGPGLVKPSQTLSLTCTVS<br>GFSLSTYGMGVG<br>WIRQPPGKGLEWIG<br>HIWWDDVKRYNPALKS<br>RVTISVDTSKNQFSLKLSSVTAADTAVYYC<br>AR<br>MGSDYDVWFDY<br>WGQGTLVTVSS | 22 |
| H5 | VB_4-28 | QVQLQESGPGLVKPSDTLSLTCAVS<br>GFSLSTYGMGVG<br>WIRQPPGKGLEWIG<br>HIWWDDVKRYNPALKS<br>RVTMSVDTSKNQFSLKLSSVTAVDTAVYY<br>CAR<br>MGSDYDVWFDY<br>WGQGTLVTVSS | 23 |
| H6 | VB_3-33 | QVQLVESGGGVVQPGRSLRLSCAAS<br>GFSLSTYGMGVG<br>WVRQAPGKGLEWVA<br>HIWWDDVKRYNPALKS<br>RFTISRDNSKNTLYLQMNSLRAEDTAVYY<br>CAR<br>MGSDYDVWFDY<br>WGQGTLVTVSS | 24 |
| H7 | C836<br>HCV-<br>region,<br>Murine<br>Parent | QVTLKESGPGILQPSQTLSLTCSFS<br>GFSLSTYGMGVG<br>WIRQPSGKGLEWLA<br>HIWWDDVKRYNPALKS<br>RLTISKDTSGSQVFLKIASVDTSDTATYYC<br>AR<br>MGSDYDVWFDY<br>GQGTLVTVSA | 3 |

The framework adapted V-regions of the heavy chain were fused to the C-kappa (light chain) and CH1-CH3 (heavy chain) of human IgG1 using methods known to those skilled in the art. A mouse-human IgG1 chimera construct was also made (Mab 167), where the murine VH region was fused to a human IgG1 at the CH1 domain and the murine VL to a human C-kappa domain, bringing the total to 16 Light and 7 Heavy chains, respectively.

Synthesis of the human framework adapted light chains and heavy chains was performed by total chemical synthesis of polynucleotide fragments which were assembled into full-length coding sequences according to methods taught in Evans, et al., See e.g., U.S. Pat. Nos. 6,521,427 and 6,670,127. The synthesized genes were inserted into the CMV promoter vector, pUNDER, and sequence confirmed. These vectors were then used in batch transient transfections or varying scale as described below.

Small-scale transfection and expression. The expression of the HFA variants was performed in a matrix format of pairing each HFA Heavy chain (Hc) with each HFA Light chain (Lc) on a small scale using HEK293 cells, resulting in 90 HFA mAbs (15 Lc×6 Hc) available for screening. The parental mouse-human chimera Lc and Hc were paired and expressed in the same manner as controls. Briefly, HEK293-E cells (Invitrogen, Carlsbad, Calif.) were plated at $1.5 \times 10^6$ viable cells per well in a 48-well plate with 0.5 ml of growth media, each DNA (Lc+Hc) pair complexed with Lipofectamine 2000 (Invitrogen), and the DNA-Lipid complex was added to duplicate wells to transfect the cells. Media, 293 SFM II (Invitrogen) with 4 mM L-Glutamine (Invitrogen), was replaced after 24 hours. The supernatants containing secreted antibody were harvested after 96 hours and filtered for assay.

Pilot Scale Transfection of HEK293-E or CHO-S cells. HEK293-E cells were plated in a Cellstack 2-layer vessel (Corning) with 200 ml of growth media at $8.0 \times 10^4$ cells per vessel. The DNA-Lipofectamine complex was made as described in the small-scale transfection method.

For CHO-S cultures, on the day of transfection cells were diluted to $7.5 \times 10^5$ cells per ml in 500 ml of media per 2 L shake flask. DNA diluted into Opti-Pro medium (Invitrogen Cat #12309) and mixed with FreeStyle Max transfection reagent (Invitrogen Cat #16447). The DNA Max complex (10 ml) was added to the flask of cells, incubated at 37° C., and supernatants harvested after 4 days.

Large scale (4-5 L), bioreactor production The day prior to transfection, cells were seeded at $2.0 \times 10^5$ cells per ml in a Cell Culture BioBundle bioreactor (Applikon, Foster City, Calif.) maintained at 37° C. with the headspace oxygen ($O_2$) monitored and controlled at 50% and pH controlled with sodium bicarbonate at pH 7.2. At the time of transfection the pH was lowered to 6.8. For the DNA-lipid complex, 1.25 mg of total DNA per transfection liter was diluted in 50 ml of Opti-Pro. Similarly, 1.25 ml of FreeStyle Max transfection reagent was diluted per transfection liter in 50 ml of Opti-Pro. The diluted DNA was mixed with the diluted FreeStyle Max reagent and incubated for 20 minutes at room temperature. The total DNA-FreeStyle Max complex (100 ml total volume) was added to the bioreactor. At the time of transfection, cells were typically at $7.0 \times 10^5$ cells per ml. The supernatant was harvested after 4 days.

Pilot scale (0.3-3.0 mgs) purifications were performed on the AKTA Xpress chromatography system and large-scale (3 mgs or greater) purifications were performed using the AKTA FPLC chromatography systems. The purification procedure for pilot and large-scale preps were identical. Cell supernatants from transiently transfected HEK293-E or CHO-S cell were clarified by centrifugation (30 min, 6000 rpm) and filtered (0.2 um PES membrane, Corning). The relative amount of IgG was determined with the Octet instrument (ForteBio). Samples transfected at large scale (5 to 20 liters) were concentrated 5-fold using an LV Centramate (Pall) concentrator. The concentrated samples were rinsed with PBS, and again 0.2 um filtered. Diluted supernatants were loaded onto an equilibrated (PBS, pH 7) HiTrap MabSelect Sure Protein A column (GE Healthcare) at a relative concentration of about 10 mg protein per ml of resin. After loading, the column was washed and protein eluted with 10 column volumes of 0.1 M Na-Acetate, pH 3. The eluted protein fractions were neutralized by elution into Tris buffer. Peak fractions were pooled, filtered (0.2 um) and dialyzed against PBS, pH 7 overnight at 4° C. The dialyzed proteins filtered (0.2 um) and the protein concentration determined by absorbance at 280 nm and 310 nm on a BioTek SynergyHT™ spectrophotometer. If necessary, the purified proteins were concentrated with a 10K MWCO centrifugal concentrator (Millipore). The quality of the purified proteins was assessed by SDS-PAGE and size exclusion HPLC (Dionex HPLC system). Endotoxin levels were measured by LAL assay (Cape Cod Associates, Cape Cod, Mass.) when required. Purified proteins were stored at 4° C. before being subjected to specificity and activity testing.

EXAMPLE 3

Assays for Evaluation of the Anti-IL-13 Antibodies

The naturally occurring variant of IL-13 with a single amino acid mutation termed IL-13 R110Q or IL-13 R130Q (SEQ ID NO: 1) was used for candidate screening. The IL-13 variant and wild-type proteins were purchased from Peprotech, Rocky Hill, N.J.

Antigen Biotinylation The IL-13 protein was biotinylated at a 4:1 molar ratio using Pierce, EZ-link NHS-LC-Biotin (#21336). To accomplish this, the biotin reagent was dissolved in an appropriate volume of Millipore water to achieve a 10 mM stock. An appropriate volume of the biotin stock is added to the IL-13 variant R130Q, Peprotech, Rocky Hill, N.J.) 200-13A) in PBS (0.1M NaHCO3, pH8.5) for 2 hours at room temperature to achieve a 4:1 molar ratio. The biotinylation reaction was quenched with 1 ml 1M Ethanolamine for 2 hours at room temperature, and excess unreacted biotin removed by dialysis overnight at 4° C. with PBS. Aliquots are snap-frozen and stored at $-80°$ C. The biotinylated IL-13 wt and variant were re-quantitated by $OD_{260}$. The biotinylated IL-13 forms (designed with "b-") were assayed by (a) activation of STATE in THP-1 cells for binding to IL-13 R$\alpha$1; and (b) binding to IL-13 R$\alpha$2 in the R$\alpha$2 (R&D Systems, Minneapolis, Minn.) via ELISA as described below.

Reference Antibodies

Several antibodies were used as reference antibodies and include: 1) mAb 167, C836 murine/human chimera, comprising SEQ ID NO: 2 and 3 V-regions; 2) mAb 62 or Fab 62 (HFA62 or HFAL62); 3) C836 human framework LC6HC2, comprising SEQ ID NO: 9 and 20 V-regions; and 4) mAb 442, human IgG1 isotype control. Multiple bioactivity assays were used to screen and define binding characteristics of the anti-IL-13 mAbs and are described below.

IL-13 Direct Binding ELISA

Black 96-well Maxisorp plates were incubated overnight at 4° C. with 100 ul goat anti-human Fc Capture Antibody at 8 ug/ml in 0.1M carbonate-bicarbonate coating buffer, washed with PBS with 0.05% Tween-20, and blocked with PBS with 1% BSA. Antibody (100 ul) test samples were diluted to 7 ng/ml in Assay Buffer (PBS with 1% BSA and 0.05% Tween-20) per well incubated at room temperature with shaking for 2 hours. After washing (5×), 100 ul biotinylated IL-13 R130Q antigen diluted to 9 ng/ml in Assay Buffer was added at room temperature with shaking for 1 hour and washing repeated. The second antibody was added (100 ul) which was conjugated to streptavidin-alkaline phosphatase, diluted to 1 ug/ml in TBS-T buffer incubated at room temperature with shaking for 30 minutes. After washing (5×), 100 ul BM Chemiluminscence substrate, equilibrated to room temperature and diluted at a ratio of 10 ul AP sustrate:100 ul enhancer:890 ul assay buffer was added and incubated at with shaking for 10 minutes. Fluorescence was read with an Envision Reader using the custom "BM Chemiluminescent" program. Data was normalized to the limit of detection and the positive control mAb, to get percent antigen binding.

Ralpha2 Binding Inhibition Assay

The Ralpha2 Binding Inhibition assay involves adsorbing purchased, soluble IL-13R-alpha2 to a plate, and measuring the ability of a test antibody to prevent binding of biotinylated IL-13—R130Q. For the assay, IL-13R$\alpha$2 (R&D systems) was absorbed to Nunc Maxisorb plates at 100 ul×300 ng/ml diluted in DPBS (30 ng) and incubated overnight at 4° C. After washing (5×, TBST+0.05% Tween-20), 100 ul total volume of sample or standard was added to each well as follows: 50 ul antibody at 200 ng/ml followed by 50 ul b-R130Q at 8 ng/ml in Assay Buffer (PBS+0.5% BSA) for 1 hour at room temperature with shaking. After washing, 100 ul of Streptavidin-Alkaline Phosphatase conjugated secondary antibody at 1 ug/ml in TBST was added and incubated 0.5 hr with shaking. After washing, 100 ul BM AttoPhos substrate, equilibrated to room temperature and diluted at a ratio of one part substrate A, to four parts substrate B and incubated at room temperature with shaking for 30 minutes. Color was allowed to develop for an additional 45 minutes and fluorescence measured using an Envision Reader. The raw data was analyzed by subtracting background well values and calculating percent inhibition by setting biotinylated-IL-13-R130Q (wells labeled bR130Q) without antibody to 0% Inhibition. Percent inhibition is calculated as: (1−((Value with antibody sample)/(biotinylated IL-13-R130Q alone))× 100%).

IgG Quantitation Using Perkin Elmer AlphaScreen®

Perkin Elmer AlphaScreen (3-AS-0004 v1) is a 384-well homogeneous bead based assay used in the quantitation of engineered mAbs and Fabs. A protein sample was added to a Protein A coated acceptor bead, an anti-Kappa Light chain antibody, and streptavidin coated donor beads. When all four components form a complex, the acceptor bead and donor bead are in close enough proximity for the donor bead to transfer a single oxygen ion to the acceptor bead, which produces a signal in the acceptor bead. The signal is measured on a Perkin-Elmer Envision plate reader. The sample was quantitated using a standard curve of a known antibody on the plate. Materials used: 384-well, White Opaque, OptiPlate (Perkin Elmer), Protein-A coated Acceptor Bead (Perkin Elmer), Streptavidin coated Donor Bead (Perkin Elmer), goat anti-human Kappa light chain-Biotin (Pierce), and Tris Buffered Saline with Tween-20 (Teknova) or Bovine Serum Albumin, Probumin Diagnostic Grade K (Millipore). The background was subtracted and the concentration is determined by fitting all dilutions to the standard curve on each plate.

IL-13R1alpha Signaling Using a Phospho-STAT6 Assay

Flow cytometric measurement of IL-13-induced Stat 6 phosphorylation in THP-1 cells is a sensitive assay for evaluating the neutralization activity of IL-13 by an antibody based on the detection of IL-13 induced Stat 6 phosphorylation (P-Stat 6) by flow-cytometry (FC). This assay allows rapid and quantitative measurement of the response of THP-1 cells to rhIL-13 with sensitivity (EC50, 332 pg/ml) which is higher than for a primary human B cell based p-Stat 6 assay (EC50, 5000 pg/ml).

THP-1 cells were obtained from ATCC (TIB-202™), passed once every 4-6 days, and maintained in complete RPMI-1640 medium. Other reagents include: Alexa Fluor 488-mouse anti-P-Stat 6 mAb (BD Transduction Laboratories™, San Diego, Calif.), Cytofix/Cytoperm™ (BD Pharmingen, San Diego, Calif.), human recombinant IL-13 (R&D System, Minneapolis, Minn.). For the assay, the cells were harvested and resuspended at $5 \times 10^5$ to $1 \times 10^6$ cells per ml in fresh complete medium. The testing reagents were serially diluted in RPMI-1640 with 10% FBS: antibodies into 8 dilutions of two- or three-fold starting from 2 mg/ml or as indicated and medium only and 25 ul of each of the antibody dilutions is transferred to a 96-well plate followed by 25 ul/well×20 ng/ml (0.5 ng) of rIL-13 and left at room temperature for 10 minutes. The activity of IL-13 or variants can be tested similarly, using two- or three-fold serial dilutions of IL-13 starting from 2 ng/ml or as indicated.

For the typical assay, THP-1 cells are added to the wells containing antibody and/or IL-13 and incubated for 15 min at 37° C. Thereafter, the cells are pelleted by centrifugation (450×g) for 3 minutes and supernatant discarded. The resuspended cells were fixed by adding Cytofix/Cytoperm buffer for 10 minutes at 37° C. followed by washing and permeabilization with cold 90% methanol for 30 minutes on ice (or cells may be stored at −20° C. for up to a month) and repelleted. The cells are stained by resuspension in staining buffer (1×PBS, 1% FBS, 0.09% $NaN_3$) containing 20 ul of Alexa Furo-anti-P-Stat 6 and incubated 1 hour at room temperature in the dark. The cells are then washed and resuspended in staining buffer for flow cytometric (FC) analysis using either a FACSCalibur or CellQuestPro (BD, San Diego, Calif.) for data acquisition and analysis. P-Stat 6 positive THP-1 cells= (the number of P-Stat 6+THP-1 cells/the number of total THP-1 cells)×100.

Biacore Assay

Affinity measurements using Surface Plasmon Resonance (SPR) were performed using a Biacore 3000 optical biosensor (Biacore). A biosensor surface was prepared by coupling anti-human IgG Fc fragment specific antibody (Jackson) to the carboxymethylated dextran surface of a CM-5 chip (Biacore) using the manufacturer instructions for amine-coupling chemistry. Approximately 20,000 RU (response units) of anti-human IgG Fc antibodies were immobilized in each of four flow cells. The kinetic experiments were performed at 25° C. in PBS running buffer (containing 0.005% surfactant P20 and 3 mM EDTA). This buffer was filtered and degassed for at least 30 minutes prior to use. Serial dilutions of IL-13 from 33 nM to 0.046 nM were prepared in running buffer. About 250 RU of tested mAb was captured on flow cells 2, 3 and 4 of the sensor chip. Flow cell 1 was used as a reference surface.

Capturing of mAb was followed by a three minute injection (association phase) of IL-13 at 50 uL/min, followed by 10 minutes of buffer flow (dissociation phase). The chip surface was regenerated by two pulses of 12 seconds injection of 100 mM $H_3PO_4$ (Sigma, Cat#7961) at 50 uL/min. The collected data were processed using BIAevaluation software, version 3.2 (Biacore). First, double reference subtraction of the data was performed by subtracting the curves generated by buffer injection from the reference-subtracted curves for analyte injections. Then kinetic analysis of the data was performed using 1:1 binding model with a global fit. The result for each mAb was reported in the format of Ka (on-rate), Kd (off-rate) and $K_D$ (affinity constant).

Determination of Antibody Solubility in PBS by Centrifugal Ultrafiltration

To determine the solubility of the various antibodies at room temperature, experiments were performed using ultrafiltration spin columns. Briefly, antibody preparations in phosphate buffered saline (PBS) buffer were added to Vivaspin-15 (15 ml) ultrafiltration spin columns (30,000 MWCO, Sartorius, Goettingen, Germany) at room temperature. The columns were spun at 3000×g for 20 minute intervals in an Eppendorf 5804R centrifuge using a swinging bucket rotor. Once the volumes were reduced to about 2 ml, the supernatant was transferred to a Vivaspin-4 (4 ml) column (30,000 MWCO) and centrifuged at 4,000×g for 20 min intervals. After sample volume was reduced to 500 ul, sample was transferred to a Vivaspin-500 column and centrifuged at 15,000×g in an Eppendorf 5415R centrifuge for 15 minutes. This was repeated until precipitation was observed. At this point, centrifugation was stopped and the sample kept at room temperature overnight to reach equilibrium. The next morning, the sample was spun to remove the precipitation and the protein concentration determined at A280 using a Nanodrop (Thermo-Fisher, Wilmington, Del.) with appropriate dilution. If the concentration was greater than 100 mg/ml, the process was stopped. If precipitation did not occur, the protein concentration was measured after every other spin. If the protein concentration was found to be greater than 100 mg/ml centrifugation was stopped. Additionally, the antibodies described herein were further screened to identify characteristics that would make a particular antibody an ideal candidate for further development. The methods used for screening these antibodies are described in U.S. patent application No. 61/022,385.

EXAMPLE 4

HFA Variants Of The Anti-IL-13 Antibody

The 90 mAbs produced from the matrix transfection of each HFA light chain variant paired with each HFA heavy chain variant (Example 2, Tables 3 and 4, respectively) were initially screened by measuring direct binding to biotinylated-IL-13 R130Q in solution and the ability to inhibit IL-13 R130Q from binding to the IL-13 Rα2 using 1.1 nM Mab and 2 nM b-IL-13 R130Q.

The binding or inhibiting activity of the recombinant Mab samples were compared to that of the chimeric mAb, Lc16Hc7 (mAb 167) comprising SEQ ID NO: 2 and SEQ ID NO: 3. The data from these screens using unpurified tissue culture supernatants from small scale transfection, determined which variants were to be scaled up for expression, purification and further evaluation (Table 5). The selected HFA mAbs were expressed in HEK293 cells at large scale and purified. They were evaluated by Biacore to determine their binding affinity for the IL-13 variant R130Q.

TABLE 5

Binding Data for Test IL-13 Antibodies

| HFA mAbs | Percent IL-13 R130Q (30 ng/ml) Binding | Percent Inhibition IL-13 R130Q (333 ng/ml) to Ra2 |
| --- | --- | --- |
| Lc15Hc2 | 94.8 | 61 |
| Lc11Hc2 | 92.2 | 51 |
| Lc14Hc2 | 91.8 | 54 |
| Lc6Hc2 | 86.1 | 59 |
| Lc5Hc2 | 85.9 | 57 |
| Lc3Hc2 | 85.3 | 50 |
| Lc4Hc2 | 84.7 | 55 |
| Lc2Hc2 | 84.0 | 52 |
| Lc8Hc2 | 81.1 | 55 |
| Lc10Hc2 | 78.9 | 57 |
| Lc15Hc1 | 76.2 | 44 |
| Lc12Hc1 | 36.4 | 26 |

TABLE 5-continued

Binding Data for Test IL-13 Antibodies

| HFA mAbs | Percent IL-13 R130Q (30 ng/ml) Binding | Percent Inhibition IL-13 R130Q (333 ng/ml) to Ra2 |
|---|---|---|
| Lc3Hc6 | 26.6 | 14 |
| Lc7Hc6 | −0.3 | 4 |
| Lc7Hc1 | −1.4 | 6 |
| Lc16Hc7 | 100 | 74 |

TABLE 6

Biacore data on selected HFA samples.

| HFA mAbs | $K_D$ by Biacore (pM) |
|---|---|
| Lc14Hc2 | 256 ± 19 |
| Lc8Hc2 | 272 ± 22 |
| Lc6Hc2 | 269 ± 24 |
| Lc3Hc2 | 246 ± 24 |
| Lc2Hc2 | 365 ± 15 |
| Lc16Hc7 (mouse-human chimera) | 54 ± 11 |
| C836 mouse mAb (parental IgG) | 52 ± 10 |

Based on these data, HFA variants Lc6Hc2 and Lc14Hc2 were chosen for affinity maturation.

EXAMPLE 5

Affinity Maturation and Production of Variants of an Anti-IL-13 Antibody

Studies of antibody-antibody complexes of known three-dimensional structure have revealed the antigen-contacting residues within CDRs, called Specificity-Determining Residues (SDRs) (Padlan, et al., 1995, FASEB J 9:133-9; Almagro 2004, J Mol. Recognit. 17: 132-143). To improve the affinity of the lead HFA variant, a random library in four SDRs of high usage for protein antigen recognition, residues H91, N92, E93, and Y94 of the L-CDR3 was used.

Two phage libraries of L-CDR3 variants were made using CDR grafted Lc6-VB_Lc6 as scaffold for library construction (SEQ ID NO: 9) called phagemid IL-13-62, and a second using Lc14 VB_L12 (SEQ ID NO: 17) designated phagemid IL-13-142. Both libraries were combined with Hc2 (SEQ ID: 20) and cloned as Fab fragments. The four residues (H91, N92, E93, and Y94) of L-CDR3 in SEQ ID NO: 9 (Lc6) and SEQ ID NO:17 (Lc14) were randomized by introducing full diversity using "NNK" codons to provide a theoretical diversity of $1.9 \times 10^5$ variants. A phagemid with the V-regions of the parent murine Mab, C836, was also constructed and designated IL-13-167.

The Fab libraries were constructed in a pIX phage display system as described in U.S. Pat. No. 6,472,147 (Scripps) and applicants co-pending application published as WO2009/085462. The phagemid IL-13-62 was expressed as a dicistronic unit containing the variable regions of IL-13Lc6 and IL-13Hc2. Construction of the library was done using methods similar to those described previously (Almagro et al., 2006. J Mol Recognit 19: 413-422). The libraries were assembled from three fragments by nested PCR composed of an N-terminal region (fragment 1) and a C-terminal region (fragment 3) in order to capture the individual N-terminal and C-terminal fragments from the parent molecule. Once generated, the outside fragments were mixed with the internal fragment targeting the respective SDRs, (fragment 2). Fragment 2 was made from degenerate oligos and used to bridge fragments 1 and 3 to generate the full-length library sequence. The full-length sequences were cloned into the respective light chain phage vector.

The libraries were panned against biotinylated IL-13 R130Q. Briefly, previous to panning, paramagnetic beads (Invitrogen, Carlsbad, Calif.) coated with streptavidin were blocked in Chemiblocker (Chemicon, Temecula, Calif.). Similarly, the L-CDR3 phage library was pre-blocked in Chemiblocker, diluted 1:1 in Tris buffered saline (TBS) with 0.05% Tween-20 (T) for 30 minutes at room temperature, followed by a pre-adsorption step, in which the L-CDR3 library was incubated with the blocked magnetic beads to remove non-specific binders. Biotinylated IL-13 variant R130Q (Peprotech, Rocky Hill, N.J.) was then added to the phage library in different concentrations (between 10 nM and 0.01 nM) for three-successive rounds of panning. Antigen-bound phage was captured using magnetic beads and rescued by addition of 1 ml exponentially growing *Escherichia coli* TG-1 cells, OD(600 nm)=0.5, and incubation at 37° C. for 30 minutes. Phage was then produced and prepared for the next round of panning. Fab-pIX was produced from crude bacterial cell lysates of TG-1 colonies A high throughput single point (10 nM) ELISA was used to rank the variants from the phage panning effort. Binding to biotinylated IL-13R130Q curves of specific SDRU variant Fabs displayed on phage pIX protein was demonstrated. Clones with a signal higher than IL-13-167 (higher affinity binders than the murine-human chimeric Fab) were chosen for Fab to Mab conversion. The ranked data for the IL-13-62 library based on SEQ ID NO: 9 and 20 is presented in Table 7A where at least 40 clones had higher affinity for IL-13 than the murine parent sequence Fab (Phage-Lc16H7). Table 7B shows comparable date for the IL-13-142 library based on SEQ ID NOS: 17 and 20 where 53 clones had higher affinity than the murine parent sequences (Lc16H7). A few clones contained mutations in the framework (as noted).

TABLE 7A

Ranked IL-13-62 Library Data

| Fab Clone | H91 | N92 | E93 | Y94 | Signal (% of Lc16Hc7) | Additional Mutation |
|---|---|---|---|---|---|---|
| | Q | D | G | del | 184 | None |
| 1H05 | Q | D | Y | G | 172 | None |
| 1C06 | H | S | W | G | 172 | None |
| 3A10 | H | V | W | G | 160 | None |
| 1C09 | H | N | E | A | 152 | Q38R |
| 1H02 | H | L | L | G | 148 | None |
| 1F05 | H | V | G | G | 144 | None |
| 1D01 | H | S | Y | G | 144 | None |
| 1G05 | Q | D | I | G | 144 | None |
| 2B07 | H | D | W | G | 144 | None |
| 4D01 | P | L | D | V | 140 | None |
| 1H06 | H | D | W | A | 139 | None |
| 3D11 | H | L | N | G | 136 | None |
| 1A05 | H | D | Y | A | 136 | None |
| 1C07 | H | E | S | G | 136 | None |
| 2A07 | H | D | P | G | 136 | None |
| 2A11 | H | S | H | G | 132 | None |
| 2C06 | H | D | del | Y | 128 | L54Q (CDR2) |
| 3C01 | H | N | F | G | 124 | None |
| 1A06 | H | E | W | G | 122 | None |
| 3E03 | H | S | I | G | 122 | None |
| 3G01 | Q | D | L | G | 122 | None |
| 3H12 | H | D | S | G | 120 | mut outside VL |
| 1A07 | H | D | N | S | 120 | None |
| 1A02 | H | S | W | A | 120 | None |
| 1D02 | H | D | W | S | 117 | S76G |
| 4B10 | H | F | W | G | 117 | None |
| 4F07 | P | I | D | A | 116 | None |
| 1D08 | H | D | W | E | 116 | None |

TABLE 7A-continued

| Ranked IL-13-62 Library Data | | | | | | |
|---|---|---|---|---|---|---|
| Fab Clone | H91 | N92 | E93 | Y94 | Signal (% of Lc16Hc7) | Additional Mutation |
| 2G06 | H | L | D | S | 112 | S56G (in CDR2) |
| 1H12 | H | D | L | G | 111 | None |
| 3F08 | H | L | M | G | 111 | None |
| 3G05 | P | L | D | S | 108 | None |
| 1B05 | H | D | R | D | 108 | None |
| 1F04 | H | S | S | G | 108 | None |
| 1F11 | H | S | V | G | 108 | None |
| 2D09 | H | N | V | G | 108 | None |
| 2E07 | P | L | E | A | 104 | None |
| 1F12 | H | N | H | G | 100 | None |
| 2D04 | Q | D | S | del | 100 | None |

TABLE 7B

| Ranked IL-13-142 Library Data | | | | | |
|---|---|---|---|---|---|
| | Amino Acid Sequence | | | | % of Lc16Hc7 |
| Phage # | H91 | N92 | E93 | Y94 | 100 |
| 68 | H | D | F | del | 397.9 |
| 54 | H | D | W | G | 360.7 |
| 75 | L | S | Y | E | 355.3 |
| 55 | H | L | T | N | 354.9 |
| 82 | H | D | V | S | 341.5 |
| 86 | H | D | T | G | 334.2 |
| 05 | H | V | S | G | 320.1 |
| 10 | H | L | W | G | 318.0 |
| 22 | H | D | P | G | 313.4 |
| 70 | H | S | W | G | 307.6 |
| 74 | Q | D | M | G | 300.7 |
| 35 | H | D | R | G | 296.2 |
| 31 | H | F | R | R | 288.3 |
| 46 | H | V | T | L | 281.2 |
| 21 | W | S | D | G | 276.5 |
| 94 | H | D | L | G | 272.5 |
| 85 | H | M | W | G | 259.3 |
| 76 | H | L | D | L | 256.5 |
| 57 | H | D | W | E | 244.8 |
| 61 | H | L | F | T | 244.7 |
| 44 | H | D | I | G | 239.7 |
| 27 | H | N | D | S | 237.7 |
| 56 | H | W | D | A | 234.4 |
| 47 | L | T | Y | E | 232.9 |
| 06 | P | L | T | H | 232.0 |
| 81 | H | D | V | G | 231.1 |
| 18 | W | D | G | G | 230.7 |
| 11 | Q | D | V | G | 229.4 |
| 32 | H | L | G | T | 228.5 |
| 93 | H | E | S | G | 223.2 |
| 01 | H | W | W | G | 221.6 |
| 71 | P | L | D | S | 208.5 |
| 16 | H | V | G | G | 206.3 |
| 43 | H | L | G | Q | 204.6 |
| 36 | H | E | L | G | 196.3 |
| 13 | H | E | W | G | 195.9 |
| 77 | H | D | F | A | 195.3 |
| 88 | H | F | W | G | 193.2 |
| 51 | H | S | A | G | 192.0 |
| 84 | H | L | I | E | 185.8 |
| 62 | Q | D | S | del | 184.9 |
| 29 | H | W | M | A | 182.4 |
| 48 | H | D | W | G | 180.5 |
| 40 | H | S | R | G | 178.7 |
| 39 | H | L | G | V | 177.9 |
| 09 | H | L | D | V | 171.3 |
| 80 | Q | D | del | Y | 163.4 |
| 15 | P | L | D | A | 154.4 |
| 78 | H | L | M | A | 154.1 |
| 65 | H | D | F | V | 147.2 |
| 83 | H | D | M | G | 145.2 |
| 30 | H | L | W | G | 139.9 |

TABLE 7B-continued

| Ranked IL-13-142 Library Data | | | | | |
|---|---|---|---|---|---|
| | Amino Acid Sequence | | | | % of Lc16Hc7 |
| Phage # | H91 | N92 | E93 | Y94 | 100 |
| 04 | Q | D | L | G | 127.2 |
| 67 | P | I | D | G | 126.7 |
| 87 | H | S | L | G | 124.9 |
| 33 | H | D | W | G | 124.4 |
| 72 | H | N | E | G | 113.8 |

Fab to MAb Conversion

Selected Fabs from the IL-13-62 library (Table 7A) were converted to full-length mAbs by restriction digest and insertion into the pUNDER vector for screening. These Lc6-based variants were paired with Hc2 (SEQ ID NO: 20) containing human IgG1 heavy chain and rescreened by small-scale transfection in HEK293 cells using crude supernatants and IL-13 (Table 8).

TABLE 8

| Screening MAbs Comprising LC6-Variants and Hc2 | | | | | | | | |
|---|---|---|---|---|---|---|---|---|
| Lc Designation | Q38 | S56 | H91 | N92 | E93 | Y94 | % Ra2 Binding Inhibition | Std Dev |
| 2B03 | — | — | — | D | Del | — | 90.6 | 1.15 |
| 3G05 | — | — | — | D | W | G | 89.5 | 0.253 |
| 3E06 | — | — | Q | D | S | DEL | 89 | 2.15 |
| 2C09 | — | — | — | E | W | G | 87.6 | 0.383 |
| 5F04 | — | — | — | D | Del | — | 87.1 | 0.785 |
| 2C05 | — | — | Q | D | L | G | 83.8 | 0.794 |
| 2E12 | — | — | — | D | W | S | 83 | 2.67 |
| 1A05 | — | — | Q | D | G | DEL | 82.7 | 0.156 |
| 1H02 | — | — | Q | D | I | G | 81.7 | 1.06 |
| 2G01 | — | — | — | F | W | G | 81.2 | 0.0718 |
| 2H01 | — | — | — | D | W | E | 80 | 1.02 |
| 2A12 | — | — | — | D | P | G | 78.5 | 1.19 |
| 5A02 | — | — | Q | D | Y | G | 78.4 | 0.955 |
| 1B01 | — | — | — | S | W | G | 77.6 | 1.72 |
| 3A09 | — | — | — | D | L | G | 76.5 | 2.18 |
| 2A03 | — | — | — | E | S | G | 75.8 | 0.621 |
| 3B06 | — | — | — | L | M | G | 74.3 | 1 |
| 2A02 | C836 LcV, (SEQ ID NO: 2) | | | | | | 73 | 2.09 |
| 5D03 | — | — | — | S | Y | G | 72.8 | 4.84 |
| 2A01 | — | — | — | S | H | G | 72.1 | 0.541 |
| 3E03 | — | — | — | — | H | G | 70.9 | 4.28 |
| 3E05 | — | — | P | L | D | T | 70.8 | 3.8 |
| 1C02 | — | — | — | V | W | G | 68.4 | 3.35 |
| 3G01 | — | — | P | L | D | V | 68.4 | 4.6 |
| 2C01 | — | — | — | S | I | G | 67.7 | 4.54 |
| 3A04 | — | — | P | L | D | S | 67 | 1.94 |
| 3G02 | — | — | — | L | N | G | 66.9 | 3.11 |
| 5G02 | — | G | — | L | D | S | 66.2 | 1.8 |
| 5H04 | — | — | — | D | Y | A | 66.1 | 2.36 |
| 5B03 | R | — | — | — | — | A | 63 | 4.37 |
| 2H09 | — | — | P | I | D | A | 62.5 | 4.99 |
| 2H08 | — | — | — | L | D | S | 62.3 | 3.97 |
| 3C06 | — | — | — | S | V | G | 62.1 | 1.09 |
| 2C04 | — | — | — | — | F | G | 61.9 | 3.46 |
| 1E03 | — | — | — | L | L | G | 61.5 | 2.06 |
| 3D01 | — | — | — | V | G | G | 58.5 | 3.14 |
| 1F03 | — | — | — | D | R | D | 57.6 | 5.5 |
| 2E04 | — | — | P | L | — | A | 56.6 | 5.08 |
| 3A05 | — | — | — | D | N | S | 55.5 | 3.9 |
| 1G02 | — | — | — | S | W | A | 55.2 | 1.49 |
| 2E01 | — | — | — | — | — | A | 53.9 | 4 |
| 2E06 | — | — | — | S | S | G | 50.2 | 2.79 |
| 3C09 | HFA Lc6(SEQ ID NO: 9) | | | | | | 34.6 | 2.43 |

The absolute IL12Ra2 binding results from the IL-13-62 library (Table 7A) and IL-13-142 library (Table 7B) cannot be directly compared in terms of magnitude of the signal as the assays were done using slightly different conditions. Variants from the 142 library were not tested in Mab format.

Site Directed Mutagenesis Targeting Specific Residues in the CDRs

While pIX phage display and panning was chosen as the mode for affinity maturation of the framework adapted C836 light chain, site-directed mutagenesis (SDM) was also used on Lc6 and Hc2. Using SDM, certain residues of the SDRs were randomized to all possible amino acids except methionine and cysteine. Conversely, any methionines or cysteines in the SDRs were removed to avoid the presence of residues susceptible to oxidation. Thus, in Hc2 (SEQ ID NO: 20) M34 and M100 were altered by SDM and these single position variants were screened for increases in binding activity along with sequences comprising additional mutations.

Briefly, about 200 light chain variants and 400 heavy chain variants of Lc6-Hc2 were generated by high throughput, site-directed mutagenesis. For the assay, each light chain variant was paired with the Hc2 sequence and screened for activity (data not shown). Similarly, each heavy chain variant was paired with Lc6 for screening of IL-13 Direct Binding and Rα2 binding competition assays with IL-13. Using this approach, several improved antibodies were identified having both the light and heavy chain variants. Many variants demonstrated improvement over the original murine antibody and others were improved compared to the HFA V-regions L6 (SEQ ID NO: 9) and H2 (SEQ ID NO: 20). Some of the enhancing light chain mutations were in the same position as the positive mutations identified from the phage variant library method. In addition, selected heavy chain variants with improved activity were combined with phage derived light chains to form complete MAbs and retested. Several of these combinations produced additive enhancement of binding affinity for IL-13 R130Q. That is the binding affinity was greater than that measured for the original murine Mab (C836) and several-fold higher as compared to the HFA V-regions, Lc6 and Hc2. These MAbs were purified and subjected to binding affinity measurements using plasmon resonance (Biacore) and more than 50 of the MAbs tested (more than 100 tested) had higher affinity for IL-13 than the original murine Mab (C836) which was about 50 pM.

Based on the Lc plus He matrix screening data, selected He variants (obtained through SDM) were paired with a L6 variant N92-, E93D of SEQ ID NO: 9 (represented as SEQ ID NO: 25) and production scaled up for purification and further analysis. These mAbs were rigorously tested for direct binding to IL-13 R130Q by Biacore analysis, for neutralizing activity by the ability to inhibit IL-13 binding to its Rα1 in the phospho-STAT6 assay, and by a Luminex based version of the ability to inhibit IL-13 R130Q from binding to its Rα2. The binding inhibition to IL-13Ra2 used 500 pg/ml b-wt IL-13 and the $IC_{50}$ values were calculated based on curves as shown in FIG. 2. The $EC_{50}$ values for the P-STAT6 assay and the $IC_{50}$ values for the Rα2 inhibition Luminex assay are presented in Table 9.

TABLE 9

Properties Of Mab Candidates Comprising Lc-2B03 (SEQ ID NO: 25) And M34 And M100 Substituted Hc2 (SEQ ID NO: 20).

| SEQ ID NO: 20 (HC) Variations | $K_D$ (pM) HEK IL-13 R130Q | $K_D$ (pM) CHO wt IL-13 | $K_D$ (pM) CHO IL-13 R130Q | Solubility PBS mg/ml | Solubility Serum mg/ml | P-STAT6 $EC_{50}$ ng/ml | Ra2 Inhib $IC_{50}$ ng/ml |
|---|---|---|---|---|---|---|---|
| M34S, M100L | 1.4 | | 18.4 | <114.8 | | | |
| M34E, M100L | 7.6 | | | | | 0.16 | 3.4 |
| M34V, M100L | 16.4 | 10.6 | 19 | 114 | 57 | 1.8 | 2.13 |
| M34V, M100L, V106I | 25.2 | | | | | | |
| M34S, M100L, V106I | 20.5 | | | | | | |
| M34E, M100L, V106I | 11.4 | | | | | 1.79 | 2.54 |
| M34S, M100L, V106I | 20.9 | | | 159 | | 1.1 | 2.25 |
| M34Q, M100L | 24.3 | | 25.1 | | | 0.87 | 1.71 |
| T31S, M34S, M100L, V106I | 15.2 | | 21.1 | | | 0.65 | 1.68 |
| T31S, M34S, M100L | 12.3 | | 10.1 | | | 0.59 | 1.72 |
| T31S, M34V, M100L | 3.7 | | 5.8 | | | 0.59 | 1.75 |

Thus, the substitutions in Lc6 (SEQ ID NO: 9) found in mAb candidates from Table 7A with framework mutations, include the variants described below for SEQ ID NO: 27.

| Lc6-Light Chain Sequence Variants (SEQ ID NO: 27; CDRs underlined) | Description of Variants |
|---|---|
| EIVLTQSPAT LSLSPGERAT | Where: |
| LSCRASKSIS KYLAWYQ$X_{38}$KP | residue 38 may be Met, Ser, Leu, Glu, |
| GQAPRLLIYS GST$X_{54}$QSGIPA 60 | Gln, or Val; |
| RFSGSGSGTD FTLTISSLEP | 54 may be Leu or Gln; |
| EDFAVYYCQQ $X_{91}X_{92}X_{93}X_{94}$PYTFGQ | 91 may be His, Gln, or Pro; |

-continued

| Lc6-Light Chain Sequence Variants (SEQ ID NO: 27; CDRs underlined) | Description of Variants |
|---|---|
| GTKLEIK 107 | 92 may be Asn, Asp, Ser, Leu, Pro, Ile, Phe, Glu, or Val; 93 may be Glu, Asp, Gly, Ser, Ile, Tyr, Tryp, Asn, His, Val, Met, Arg, Leu, Phe, Pro or be absent; and 94 may be Tyr, Gly, Ser, Ala, Val, Phe, Thr, Glu, or be absent. |

Site directed mutagenesis was used to create additional variants with changes in Hc2 (SEQ ID NO: 20) CDR 1 ($_{26}$GFSLSTYGMGVG$_{37}$) and CDR3 ($_{100}$MGSDYDVWFDY$_{110}$). The variants of the heavy chain variable domain producing high affinity IL-13 binding can include those of (SEQ ID NO: 28).

| Hc2 Heavy Chain Sequence Variants (SEQ ID NO: 28; CDRs underlined) | Description of Variants |
|---|---|
| QVTLKESGPV LVKPTETLTL | Where residue 31 may be T or S; |
| TCTVSGFSLS $X_{31}$YG$X_{34}$GVGWIR | 34 may be Met, Ser, Leu, Glu, Gln, or |
| QPPGKALEWL AHIWWDDVKR 60 | Val; |
| YNPALKSRLT ISKDTSKSQV | 100 may be Met or Leu; and |
| VLTMTNMDPV DTATYYCAR$X_{100}$ | 106 may be Val or Ile. |
| GSDYD$X_{106}$WFDY WGQGTLVTVS S | |
| 121 | |

Thus, a heavy chain variable region of SEQ ID NO: 28, and the variants described above, may be used to engineer an antibody in combination with a second antigen binding domain comprising the variants of in the L-CDR3 as shown in Formula I:

Q-Q-Xaa$_1$-Xaa$_2$-Xaa$_3$-Xaa$_4$-P-Y-T, (SEQ ID NO: 29)

where Xaa$_1$ may be His, Gln, or Pro;

Xaa$_2$ may be Asn, Asp, Ser, Leu, Pro, Ile, Phe, Glu, or Val;

Xaa$_3$ may be Glu, Asp, Gly, Ser, Ile, Tyr, Tryp, Asn, His, Val, Met, Arg, Leu, Phe, Pro or be absent; and Xaa$_4$ may be Tyr, Gly, Ser, Ala, Val, Phe, Thr, Glu, or be absent.

The complementarity determining regions (CDRs) from the mouse monoclonal antibody, C836 were adapted into 15 human light and six heavy chain antibody frameworks providing antibodies that that bind human IL-13 R130Q and wild-type human IL-13 with high affinity. HFA light chains 2, 3, 6, 8, 14 (SEQ ID NOs: 5, 6, 9, and 17) and heavy chain 2 (SEQ ID NO: 20) produced MAbs with highly desirable bioactivity and high affinity. The resulting human framework adapted antibodies are expected to have lower immunogenicity if administered to human patients and therefore provide a longer plasma half-life than their fully murine or chimeric counterparts.

The affinity ($K_D$) of the wild type, full-length mouse mAb C836, was determined to be about 50 pM and similar to that of the mouse V-region-human C-region chimera (Lc16Hc7) as measured by Biacore. The adaptation of the CDRs from the C836 mAb into human antibody frameworks decreased the binding $K_D$ to the antigen by about 5-fold from, to about 250 pM (Table 6) which is typical for a simple CDR-grafted chimera. High throughput matrix screening of a phage Fab library and de novo synthesis of new antibody chains and vector construction for transient transfection enabled screening of numerous Fabs, as well as full-length MAbs, comprising heavy and light V-region combinations, for relative binding.

In a second step, the binding affinities of selected human framework adapted mAbs were matured by focusing variegation to selective residues called SDRs using both phage Fab-libraries and site directed mutagenesis. From these efforts, mAbs having a single light chain sequence paired with 11 variants of Hc2 (SEQ ID NO: 20) sequence were expressed in CHO and HEK293 cells and showed binding affinities by Biacore analysis for IL-13 R130Q and wild-type IL-13 of less than 50 pM (Table 9). These antibodies: 1) neutralized IL-13 function by inhibiting IL-13 R130Q and wild-type IL-13 from binding to the IL-13 receptor Rα1; inhibited the phosphorylation of the STAT-6 transcription factor, known to be activated by signaling through the IL-13 Ra1/IL-4 receptor complex; and 3) inhibited binding of IL-13 R130Q and wild type IL-13 to the IL-13 receptor Rα2.

Biophysical characterization indicated that several species show solubility at greater than 100 mg/ml in PBS and greater than 50 mg/ml in human serum. Thus, these active, engineered mAbs have properties that are consistent with desirable properties typically seen in a therapeutic molecule for use in the treatment of IL-13-mediated diseases.

In addition to mAbs made by combining the light chain designated 2B03 (SEQ ID NO: 25) with the Hc2 CDR variants such as SEQ ID NO: 26, other light chain variants of SEQ ID NO: 9 and 17 combined with the heavy chain variants of SEQ ID NO: 20 as shown in Table 9 can be prepared. Thus, large number of high affinity, IL-13 immunospecific variants mAbs are possible based upon these discoveries and the teachings herein. For example, these include the variants set forth in SEQ ID NOs: 25 and 26.

The Hc and Lc combination represented by Mab M1295 comprising variable regions SEQ ID NO: 25 and 26 is of particular interest as having a heavy chain framework that is amenable to therapeutic development. Removal of methionine in heavy chain CDR 1 and CDR3 (residues 34 and 100) reduces the chances of oxidation and makes these sequences ideal for therapeutic development. Antibodies having reduced methionine content reduced are hoped to exhibit improved stability to oxidation.

EXAMPLE 6

Epitope and Paratope Analysis of Anti-IL-13 Binding Domains

Epitope mapping using X-ray crystallography of Fabs related to C836 (comprising SEQ ID NO: 2 and 3), the CDR-grafted human framework adapted variant HFAL62 (comprising SEQ ID NO: 9 and 20), and the V-region affinity matured variant M1295 (comprising SEQ ID NO: 25 and 26) bound to IL-13 (SEQ ID NO: 1) was performed and the results were compared.

A His-tagged chimeric version of the C836 Fab was expressed in CHO cells and purified using affinity and size-exclusion chromatography. The Fab fragments of HFAL62 and M1295 were prepared by papain cleavage of the corresponding mAbs and purified using affinity and size-exclusion chromatography. Recombinant human IL-13 was purchased from R&D Systems (Cat. No. 213-IL/CF). The IL-13-Fab complexes were prepared by mixing Fab with excess IL-13 at a molar ratio of 1:1.2. The mixture was incubated for 20 minutes at room temperature, concentrated, and separated from the uncomplexed species using size-exclusion chromatography.

Crystallization was carried out using the vapor-diffusion hanging-drop method at 20° C. The crystals of C836:IL-13 were obtained from 20% PEG 3350, 0.2 M sodium tartrate, 0.1 M HEPES, pH 7.5. HFAL62:IL-13 crystals were obtained from 14% PEG 3350, 0.2 M ammonium tartrate, 0.1 M MES, pH 6.5. M1295:IL-13 crystals were obtained from 25% PEG 8K, 0.1 M sodium acetate, pH 4.5. For X-ray data collection, one crystal of each complex was soaked for a few seconds in the corresponding mother liquor supplemented with 20% glycerol. Diffraction data were collected and processed using a Rigaku MicroMax™-007HF X-ray generator equipped with a Saturn 944 CCD detector, and an X-Stream™ 2000 cryo-cooling system (Rigaku, Woodlands, Tex.).

The crystal structures of the three complexes, C836:IL-13, HFAL62:IL-13, and M1295:IL-13, were determined at 2.0 Å, 1.9 Å, and 2.8 Å resolution, respectively, and were refined to the crystallographic R-factor of 22.4%, 18.6%, and 19.7%, respectively. In all three structures, the antibody-antigen interface is clearly defined in the electron density.

Each of the three Fabs (C836, HFAL62 and M1295) binds IL-13 at the surface of helices A and D close to N- and C-termini of the IL-13 polypeptide chain. The antibody-antigen interface covers about 600 Å$^2$ on each of the interacting molecules. Residues in contact are defined using a 4 Å cut-off interatomic distance. Using this definition, the epitope recognized by these antibodies includes 8 residues of IL-13, three from helix A (Arg10, Ile13, Glu14) and 5 residues from helix D (Leu100, Lys103, Phe106, Arg107, Glu108). Based on the number of contacts, Arg10 and Arg107 appear to be key residues of the epitope.

The paratope in C836 includes 12 residues that interact with IL-13 (based on 4 Å cut-off for interatomic distance) residing within each of the six CDRs except L-CDR2. The paratope includes 3 residues from the L chain (Tyr32, His91, Asn92 of SEQ ID NO: 2) and 9 residues from the H chain (Tyr32, Trp54, Trp55, Asp56, Val58, Arg60, Asp103, Tyr104, Asp105 of SEQ ID NO: 3). Based on the number of contacts, the principle recognition CDRs are H2 and H3. The anchor residue in the light chain is Tyr32, which stacks against Arg10 and forms a hydrogen bond to Glu14 of IL-13. The only contact with L-CDR3 is the hydrogen bond between Arg10 (IL-13) and the main-chain carbonyl group of His91. The side chains of residues in L-CDR3 do not appear to directly interact with IL-13.

The HFAL62 epitope and paratope residues are identical to those for C836.

M1295 comprises altered residues in L-CDR3 (SEQ ID NO: 25) as compared to HFAL62, where residues Asn92-Glu93 were replaced by Asp92, i.e., one residue was deleted and one mutated. Comparison of the M1295 and HFAL62 crystal structures in complex with IL-13 indicates no significant conformational changes occurred in the other CDRs. The deletion in L-CDR3 resulted in a shorter loop so that the introduced Asp92 residue occupies the space previously held by the Asn-Glu pair, whereas the flanking residues His91 and Tyr94 are approximately in the same positions. These changes allowed for additional contacts with IL-13. LC Asp92 of SEQ ID NO: 25, forms a salt bridge with a key epitope residue Arg10 (SEQ ID NO: 1). This salt bridge does not exist in HFAL62 because a potential partner (Glu93) points away from Arg10. Another new contact is the hydrogen bond between LC Asp92 and Ser6 at the N-terminus of IL-13. This interaction extends the epitope since Ser6 was not in contact with either HFAL62 or C836. In total, the IL-13 epitope bound by M1295 includes 9 residues of IL-13 (Ser6, Arg10, Ile13, Glu14, Leu100, Lys103, Phe106, Arg107, Glu108). The paratope of M1295 includes 3 residues from the L chain (Tyr32, His91, Asp92) and 9 residues from the H chain (Tyr32, Trp54, Trp55, Asp56, Val58, Arg60, Asp103, Tyr104, Asp105).

EXAMPLE 7

Alanine Scanning

In addition to crystallography, described herein is an alanine scanning mutagenesis study of the C836 heavy and light chain variable regions, to determine the residues of the variable domain(s) that are important in binding to IL-13.

Residues of antibody variable domains in contact with antigens examined in 59 complexes and described as specificity determining residues (SDR) were selected for mutagenesis. The residues were 27-36, 46-56, and 89-97 of the C836 light chain (SEQ ID NO: 2) and residues 27-39, 49-60, and 100-111 of the heavy chain (SEQ ID NO: 3). The variants were tested in the IL-13R-alpha2 solid phase assay as described in Example 2 at six concentrations using serial 3-fold dilutions starting from 1 ug/ml. The activities were normalized to the wild-type Mab.

Based on how IL-13R-alpha2 binding changed at a low nanomolar concentration of antibody relative to the wild-type antibody, or whether binding was unaffected or actually enhanced by the alanine substitution, the residues were categorized (in order of importance) as "critical", "important", or "irrelevant" for binding to IL-13.

Critical in binding: Light: Y32, Q89, Q90, and H91. Heavy: G33, H52, V58, R60, M100, G101, S102, D103, Y104, D105, and W107.

Important for binding: Light: K31, Y49, N92, E93, and Y96. Heavy: F27, L29, Y32, M34, G35, L50, 153, W54, D56, and V106.

Irrelevant for binding: Light: K27, S28, I29, S30, L33, S50, G51, S52, T53, L54, Q55, S56, Y94, and P95. Heavy: S28, S30, T31, W49, D57, and K59.

Overall, the heavy chain had more residues involved in binding (i.e., categorized as either critical or important for binding) relative to the light chain residues. That supports the observation that several different light chain frameworks could produce IL-13 antibodies that effectively bind IL-13. For example, the combination of L3 (SEQ ID NO: 6), L6 (SEQ ID NO: 9), and L14 (SEQ ID NO: 17) combined with H2 (SEQ ID NO: 20) have similar $K_d$ values of about 250 pM. In contrast, only three mutations in the framework region of the heavy chain (SEQ ID NO: 3) at 32 and 31 caused a 2-fold decrease in $K_d$; from 250 pM to 500 pM, respectively.

It was found that 20 residues of the 51 residues mutated to alanine form a core of residues involved in binding, and 15 other residues proximal to critical residues are important for binding.

Taken together with the evidence from the crystallography studies (Example 6), the residues determined to be involved in binding help further define the residues of the paratope of the antibodies of the invention as well as the potential for modification to the frameworks that would result in active variants.

EXAMPLE 8

Bioactivity Of A Humanized Anti-IL-13 Antibody

M1295 was converted to a fully human IgG1 antibody and was evaluated for biologic activity in a rat model of allergic airway inflammation. Norway Brown rats sensitized and subsequently challenged with ovalbumin (ova) protein yielded an allergic response in the airways marked by increased eosinophil recruitment to the lung, and an increase in airway hyperresponsiveness (AHR) as determined by changes in lung resistance in response to challenge with methacholine (MCh), a non-selective muscarinic receptor agonist. Rats treated with M1295 IgG1 during the challenge phase of the allergic response, after systemic sensitization to ovalbumin, demonstrated a dose-dependent decrease in total cells in bronchoalveolar lavage (BAL) fluid. On Days 0, 14 and 21; 48 rats were sensitized to OVA using a series of injections of OVA and alum to establish a prolonged inflammatory response. Specifically, rats were sensitized by subcutaneous injection of 0.5 ml of a solution of OVA (100 mg/ml) mixed with aluminum hydroxide (4.28 mg/ml) in sterile solution (0.9% NaCl) with the exception of Group 1, the non-sensitized control, which was mock treated with 0.5 ml sterile 0.9% NaCl using the same protocol. All animals with the exception of the Group 1 control were then challenged with OVA (1 mg/kg) on experimental days 23, 25, and 28 by intratracheal (IT) instillation to elicit an ova-specific allergic response in the airways.

For the study, 48 rats were divided into 6 groups of 8 individuals. Group 1 was mock-sensitized and challenged with PBS and treated with vehicle. Group 2 was sensitized with ova and treated only with vehicle. Group 3 was sensitized with ova and treated with budesonide the day before and the day of OVA challenge (1 mg/kg/dose, IT). Groups 4-6 were treated with ascending doses of M1295 IgG1 (1 mg/kg, 3 mg/kg and 10 mg/kg) by intravenous injection after the sensitization phase, during the challenge phase, starting on study day 21 (afternoon after last OVA-Alum injection), and on study day 27.

On day 29, animals were subjected to pulmonary function testing in response to challenge with methacholine. After baseline measurements of resistance and compliance, increasing doses of methacholine (Mch; 6, 12, 25, 50, and 100 mg/ml in nebulizer) were delivered via aerosol and lung resistance and compliance were measured. Airway resistance was calculated for each concentration of methacholine and the average+SEM plotted for all treatment groups.

Animals were euthanized and BAL fluid recovered for determination of infiltrating cells, specifically eosinophil recruitment to the BAL. In addition to the primary endpoints of AHR and eosinophil recruitment to the BAL, lung tissue samples were collected for routine histological analyses including H&E staining and assessment of mucus production.

Changes in MCh induced airway resistance were evaluated using two-way ANOVA with Bonferonni multiple comparisons post test. Changes in BAL cell numbers, antibody levels, cytokines levels and pathology scores were made using ANOVA with an appropriate multiple comparison test. A value of $p<0.05$ is considered significant.

There was a marked dose-dependent decrease in eosinophil, lymphocyte, macrophage and neutrophil cell numbers in the groups of rats treated with M1295 IgG1 as compared to the saline-treated ova-sensitized animals. Relative percentages of eosinophils were markedly reduced, with numbers approximately 50% lower in animals treated with all doses of M1295 IgG1 compared to the saline-treated ova-sensitized animals. Although the decrease in cell recruitment to the lung and the decrease in the relative percentage of eosinophils did not reach statistical significance, the overall trends indicate biological activity of M1295 IgG1 in the rat.

With respect to airway hyperresponsiveness, animals treated with 10 mg/kg M1295 IgG1 showed a statistical significant decrease ($p<0.01$) in peak airway resistance following repeated MCh challenges 24 hours following the last lung OVA challenge, and baseline airway resistance ($p<0.05$) just prior to ascending challenge with MCh, relative to the saline-treated ova-sensitized animals.

The study confirms that M1295 IgG1 is biologically active as determined by a dose-dependent impact on parameters associated with allergic response and inflammation.

EXAMPLE 9

Use Of A Humanized Anti-IL-13 Antibody to Treat Human Disease

Preclinical studies demonstrate the functional effects of M1295-mediated neutralization of human IL-13 in human cell based in vitro assays using mechanistically relevant endpoints associated with the pathogenesis of asthma, atopic dermatitis, and eosinophil-mediated disease. Results confirm the functional effects of M1295 and antibody fragments comprising related binding regions as determined by inhibition of IL-13-mediated STATE phosphorylation, inhibition of IL-13-mediated induction of cell homing chemokines CCL2 and CCL26, and inhibition of IL-13-mediated CD23 modulation.

This data, in addition to a broad set of published data assessing the role of the IL-13 pathway in atopic and non-atopic disease, demonstrate that IL-13 is an important immune modulator and has a pivotal role in asthma, atopic dermatitis and eosinophil-mediated disease. Preclinical data support the hypothesis that antagonism of IL-13 will result in a reduction of downstream signaling events associated with type II inflammatory responses, providing evidence that anti-IL-13 therapy intervention may be beneficial in patients with clinical manifestations associated with these diseases.

Study of M1295 and antibody fragments comprising related binding regions will explore a wide range of doses (0.1 mg/kg, 0.3 mg/kg, 1.0 mg/kg, 3.0 mg/kg, and 10.0 mg/kg), including doses that may potentially be efficacious in subjects with asthma. The range of doses to be evaluated in this Phase 1 study is based on in vitro neutralization of human IL-13 bioactivity, toxicity and pharmacokinetic data in rats and cynomolgus monkeys and clinical experience with IMA-638, an anti-IL-13 mAb that binds to human IL-13 with high affinity.

---

What is claimed:

1. An isolated monoclonal antibody comprising the variable light chain of SEQ ID NO: 9, and the variable heavy chain of SEQ ID NO: 20.

2. The monoclonal antibody of claim 1 wherein said variable light chain of SEQ ID NO: 9 further comprises changes at the residues selected from the group consisting of a position 91 histidine, a position 92 asparagine, a position 93 glutamic acid, and a position 94 tyrosine.

3. The monoclonal antibody of claim 2 wherein said residues selected from the group consisting of a position 91 histidine, a position 92 asparagine, a position 93 glutamic acid, and a position 94 tyrosine are changed to different amino acids or deleted as follows:

| Histidine Pos. 91 | Asparagine Pos. 92 | Glutamic Acid Pos. 93 | Tyrosine Pos. 94 |
|---|---|---|---|
| Q | D | G | deleted |
| Q | D | Y | G |
| H | S | W | G |
| H | V | W | G |
| H | N | E | A |
| H | L | L | G |
| H | V | G | G |
| H | S | Y | G |
| Q | D | I | G |
| H | D | W | G |
| P | L | D | V |
| H | D | W | A |
| H | L | N | G |
| H | D | Y | A |
| H | E | S | G |
| H | D | P | G |
| H | S | H | G |
| H | D | deleted | Y |
| H | N | F | G |
| H | E | W | G |
| H | S | I | G |
| Q | D | L | G |
| H | D | S | G |
| H | D | N | S |
| H | S | W | A |
| H | D | W | S |
| H | F | W | G |
| P | I | D | A |
| H | D | W | E |
| H | L | D | S |
| H | D | L | G |
| H | L | M | G |
| P | L | D | S |
| H | D | R | D |
| H | S | S | G |
| H | S | V | G |
| H | N | V | G |
| P | L | E | A |
| H | N | H | G |
| Q | D | S | deleted |
| H | D | F | deleted |
| H | D | W | G |
| L | S | Y | E |
| H | L | T | N |
| H | D | V | S |
| H | D | T | G |
| H | V | S | G |
| H | L | W | G |
| H | D | P | G |
| H | S | W | G |
| Q | D | M | G |
| H | D | R | G |
| H | F | R | R |
| H | V | T | L |
| W | S | D | G |
| H | D | L | G |
| H | M | W | G |
| H | L | D | L |
| H | D | W | E |
| H | L | F | T |
| H | D | I | G |
| H | N | D | S |
| H | W | D | A |
| L | T | Y | E |
| P | L | T | H |
| H | D | V | G |
| W | D | G | G |
| Q | D | V | G |
| H | L | G | T |
| H | E | S | G |

-continued

| Histidine Pos. 91 | Asparagine Pos. 92 | Glutamic Acid Pos. 93 | Tyrosine Pos. 94 |
|---|---|---|---|
| H | W | W | G |
| P | L | D | S |
| H | V | G | G |
| H | L | G | Q |
| H | E | L | G |
| H | E | W | G |
| H | D | F | A |
| H | F | W | G |
| H | S | A | G |
| H | L | I | E |
| Q | D | S | del |
| H | W | M | A |
| H | D | W | G |
| H | S | R | G |
| H | L | G | V |
| H | L | D | V |
| Q | D | deleted | Y |
| P | L | D | A |
| H | L | M | A |
| H | D | F | V |
| H | D | M | G |
| H | L | W | G |
| Q | D | L | G |
| P | I | D | G |
| H | S | L | G |
| H | D | W | G |
| H | N | E | G. |

4. The monoclonal antibody of claim 1 wherein said heavy chain of SEQ ID NO: 20 further comprises changes at the residues selected from the group consisting of a position 31 threonine, a position 34 methionine, a position 100 methionine, and a position 106 valine.

5. The monoclonal antibody of claim 4 wherein said residues selected from the group consisting of a position 31 threonine, a position 34 methionine, a position 100 methionine, and a position 106 valine are changed to different amino acids or deleted as follows:

| Threonine Pos. 31 | Methionine Pos. 34 | Methionine Pos. 100 | Valine Pos. 106 |
|---|---|---|---|
| T | S | L | V |
| T | E | L | V |
| T | V | L | V |
| T | V | L | I |
| T | S | L | I |
| T | E | L | I |
| T | Q | L | V |
| S | S | L | I |
| S | S | L | V |
| S | V | L | V. |

* * * * *